United States Patent
Rogowski et al.

(10) Patent No.: US 12,083,090 B2
(45) Date of Patent: Sep. 10, 2024

(54) METHODS OF USING LOW-DOSE DOXEPIN FOR THE IMPROVEMENT OF SLEEP

(71) Applicants: Currax Pharmaceuticals LLC, Morristown, NJ (US); ProCom One, Inc., San Marcos, TX (US)

(72) Inventors: Roberta L. Rogowski, Rancho Santa Fe, CA (US); Susan E. Dubé, Carlsbad, CA (US); Philip Jochelson, San Diego, CA (US); Neil B. Kavey, Chappaqua, NY (US)

(73) Assignees: Currax Pharmaceuticals LLC, Morristown, NJ (US); ProCom One, Inc., San Marcos, TX (US)

( * ) Notice: Subject to any disclaimer, the term of this patent is extended or adjusted under 35 U.S.C. 154(b) by 0 days.

(21) Appl. No.: 16/876,446

(22) Filed: May 18, 2020

(65) Prior Publication Data

US 2020/0345680 A1   Nov. 5, 2020

Related U.S. Application Data

(63) Continuation of application No. 16/363,128, filed on Mar. 25, 2019, now Pat. No. 10,653,662, which is a continuation of application No. 15/864,440, filed on Jan. 8, 2018, now Pat. No. 10,238,620, which is a continuation of application No. 15/344,710, filed on Nov. 7, 2016, now Pat. No. 9,861,607, which is a continuation of application No. 14/804,595, filed on Jul. 21, 2015, now Pat. No. 9,486,437, which is a continuation of application No. 13/492,559, filed on Jun. 8, 2012, now Pat. No. 9,107,898, which is a continuation of application No. 11/804,720, filed on May 18, 2007, now Pat. No. 8,513,299.

(60) Provisional application No. 60/801,824, filed on May 19, 2006, provisional application No. 60/833,319, filed on Jul. 25, 2006.

(51) Int. Cl.
*A61K 31/335* (2006.01)
*A61P 25/20* (2006.01)

(52) U.S. Cl.
CPC .................................. *A61K 31/335* (2013.01)

(58) Field of Classification Search
CPC ........ A61K 31/335; A61P 25/00; A61P 25/20; A61P 43/00
See application file for complete search history.

(56) References Cited

U.S. PATENT DOCUMENTS

| | | | | |
|---|---|---|---|---|
| 5,502,047 A | * | 3/1996 | Kavey | A61K 31/00 514/183 |
| 6,211,229 B1 | * | 4/2001 | Kavey | A61K 31/13 514/217 |
| 6,358,944 B1 | * | 3/2002 | Lederman | A61P 25/22 514/220 |
| 2004/0097488 A1 | * | 5/2004 | Bernstein | A23L 27/13 514/220 |

FOREIGN PATENT DOCUMENTS

WO   WO-2004045528 A2  *  6/2004  ............. A23L 27/13

OTHER PUBLICATIONS

Wyatt et al., Applied Spectroscopy, publ. 1986, vol. 40(4), pp. 538-541 (Year: 1986).*
McCall, Prim. Care Companion J. Clin. Psych., vol. 6, pp. 9-20, publ. 2004 (Year: 2004).*

* cited by examiner

*Primary Examiner* — Sarah Pihonak
(74) *Attorney, Agent, or Firm* — Servilla Whitney LLC

(57) ABSTRACT

Methods of preventing early awakenings, and improving sleep efficiency in hours 7 and 8 of a period of sleep, by administration of low doses of doxepin (e.g., 1-6 mg).

13 Claims, 8 Drawing Sheets

PSG Parameters

DOXEPIN PLASMA PROFILE CONCENTRATIONS (ng/mL)

FIG. 5 DOXEPIN Phase 3 Adult Sleep Efficiency (SE) – by Hour Night 1

[1]Lichstein et al, 2004; Epidemiology of sleep: Age, gender, and ethnicity.

METHODS OF USING LOW-DOSE DOXEPIN FOR THE IMPROVEMENT OF SLEEP

RELATED APPLICATIONS

This application is a continuation of application Ser. No. 16/363,128, filed Mar. 25, 2019, which is a continuation of application Ser. No. 15/864,440, filed Jan. 8, 2018, now U.S. Pat. No. 10,238,620, which is a continuation of application Ser. No. 15/344,710, filed Nov. 7, 2016, now U.S. Pat. No. 9,861,607, which is a continuation of application Ser. No. 14/804,595, filed Jul. 21, 2015, now U.S. Pat. No. 9,486,437, which is a continuation of application Ser. No. 13/492,559, filed Jun. 8, 2012, now U.S. Pat. No. 9,107,898, which is a continuation of application Ser. No. 11/804,720, filed May 18, 2007, now U.S. Pat. No. 8,513,299, which claims priority under 35 U.S.C. 119(e) to U.S. Provisional Application Nos. 60/801,824, filed May 19, 2006; and 60/833,319, filed Jul. 25, 2006; the entire contents of each of which are incorporated herein by reference.

FIELD OF INVENTION

The present invention relates to the use of low doses of doxepin (e.g., 1-6 milligrams) to improve sleep, including sleep efficiency and early awakening in an individual.

BACKGROUND OF THE INVENTION

Sleep is essential for health and quality of life. Insomnia is a growing health problem in the United States. It is believed that more than 10-15 million people suffer from chronic insomnia and up to an additional 70 million people suffer from some form of insomnia each year. Insomnia is a condition characterized by difficulty falling asleep (sleep onset), waking frequently during the night (fragmented sleep), waking too early (premature final awakening), and/or waking up feeling un-refreshed. In the National Sleep Foundation's (NSF) Sleep in America Poll 2005, 42% of survey respondents reported that they awoke frequently during the night, 22% of adults reported waking too early and not being able to return to sleep and 38% reported waking and feeling un-refreshed.

Sleep maintenance difficulty is the most commonly reported symptom in primary care patients with chronic insomnia, and is the most common complaint in depressed patients, medically ill populations, especially those with pain symptoms, and in the elderly.

Medications commonly used to treat sleep disorders, such as insomnia, include sedative antidepressants, antihistamines, benzodiazepines, and non-benzodiazepine hypnotics.

Although there have been several advances in pharmaceutical treatments for insomnia, it is often hard to find an ideal drug for treating particular forms of insomnia. One common problem is early termination of sleep or premature final awakening. For example, many individuals may wake prematurely and not fall back asleep, thereby failing to achieve a full night of sleep. Many drugs that are effective in inducing or expediting sleep initiation do not provide much effect in maintaining sleep, particularly through the eighth and final hour of sleep period. Drugs that are sufficiently powerful to induce a full eight hours sleep often cause serious hangover effects, i.e., the patient has difficulty awakening and/or feels sedated, sleepy, or disoriented and may demonstrate impairment of psychomotor function.

In addition to patients having difficulty with early termination of sleep during the last 60, 90, or 120 minutes of an 8 hour sleep period, other patients have problems with fragmented or disrupted sleep. In other words, those patients awaken one or more times during that time period, then fall asleep again. Such fragmented sleep patterns detract from a feeling of restfulness, and make it less likely that the patient will enjoy restful sleep.

Both groups of patients would benefit greatly from a drug that addresses their particular sleep deficiency.

Doxepin is a tricyclic antidepressant that is known to have beneficial effects in treating insomnia. See, e.g., U.S. Pat. Nos. 5,502,047 and 6,211,229. However, prior to the present invention, doxepin was not known to have particular efficacy in treating premature termination of sleep at the end of an 8 hour sleep period, nor was it known to be efficacious in treating those patients with disturbed sleep patterns during the final 60, 90, or 120 minutes of an 8-hour sleep period. The mean half-life of doxepin is 17 hours, and the half-life of its major active metabolite, desmethyldoxepin, is 51 hours. Thus, when taken at the start of a sleep cycle, a majority of the drug or active metabolite should still be present in the body at the end of the sleep cycle. As a result, it would be expected that dosages of doxepin that are sufficient to address premature final awakenings or last-hour sleep efficiency in the elderly would also cause post-sleep sedation or other undesirable side effects.

The present invention describes the surprising ability of doxepin to treat last-hour sleep efficiency and premature final awakenings in patients, without untoward side effects.

SUMMARY OF THE INVENTION

Some embodiments provide methods for reducing or preventing early awakenings in a patient in need thereof. In some embodiments the methods can include identifying a patient having a sleep disorder in which, for a given 8 hour period of desired sleep, the patient experiences a sleep period that terminates during the final 60 minutes of said period; and administering to the patient, prior to the sleep period, doxepin, a pharmaceutically accept salt thereof, or a prodrug thereof in a dosage between 1 milligram (mg) and 6 mg that can be effective to lengthen the sleep period. In some aspects of the embodiment, the patient can be identified as experiencing a sleep period that terminates during the final 45 minutes of said period. In some aspects of the embodiment, the patient can be identified as experiencing a sleep period that terminates during the final 30 minutes of said period. In some embodiments, the sleep period can be lengthened to terminate during or after hour 7 of said period. In some embodiments, the sleep period can be lengthened to terminate during or after hour 7.5 of said period. In some aspects, the patient can be additionally identified as in need of reducing wake time after sleep. In another embodiment, the patient suffers from chronic or non-chronic insomnia. In yet another embodiment, the patient suffers from transient insomnia.

Some embodiments provide methods for decreasing fragmented sleep in the 8th hour of a sleep period for a patient. In some embodiments the methods include identifying a patient suffering from fragmented sleep during the 8th hour of a sleep period; and administering to the patient doxepin, a pharmaceutically acceptable salt or prodrug thereof in a dosage between about 1 mg and 6 mg. In some embodiments, the dosage of doxepin can be, for example, about 1 mg, 3 mg or 6 mg. Thus, in one aspect the dosage of doxepin can be about 1 mg. In one aspect, the dosage of doxepin can be about 3 mg. In one aspect, the dosage of doxepin is about 6 mg. In another embodiment, the patient suffers from chronic or non-chronic insomnia. In yet another embodiment, the patient suffers from transient insomnia.

Some embodiments provide methods for treating a sleep disorder, comprising identifying a patient suffering from a transient insomnia comprising a sleep deficiency associated with one or more of LPS, WASO, TST, TWT, SE, latency to Stage 2 sleep, WTDS, or WTAS; and administering to the patient doxepin, a pharmaceutically acceptable salt or prodrug thereof in a dosage between about 0.5 mg and 6 mg. In one embodiment, the dosage of doxepin is about 1 mg, 3 mg or 6 mg. In other embodiments, the dosage of doxepin is about 0.5 mg, 1 mg, 3 mg or 6 mg.

DETAILED DESCRIPTION OF THE INVENTION

Figure 1:
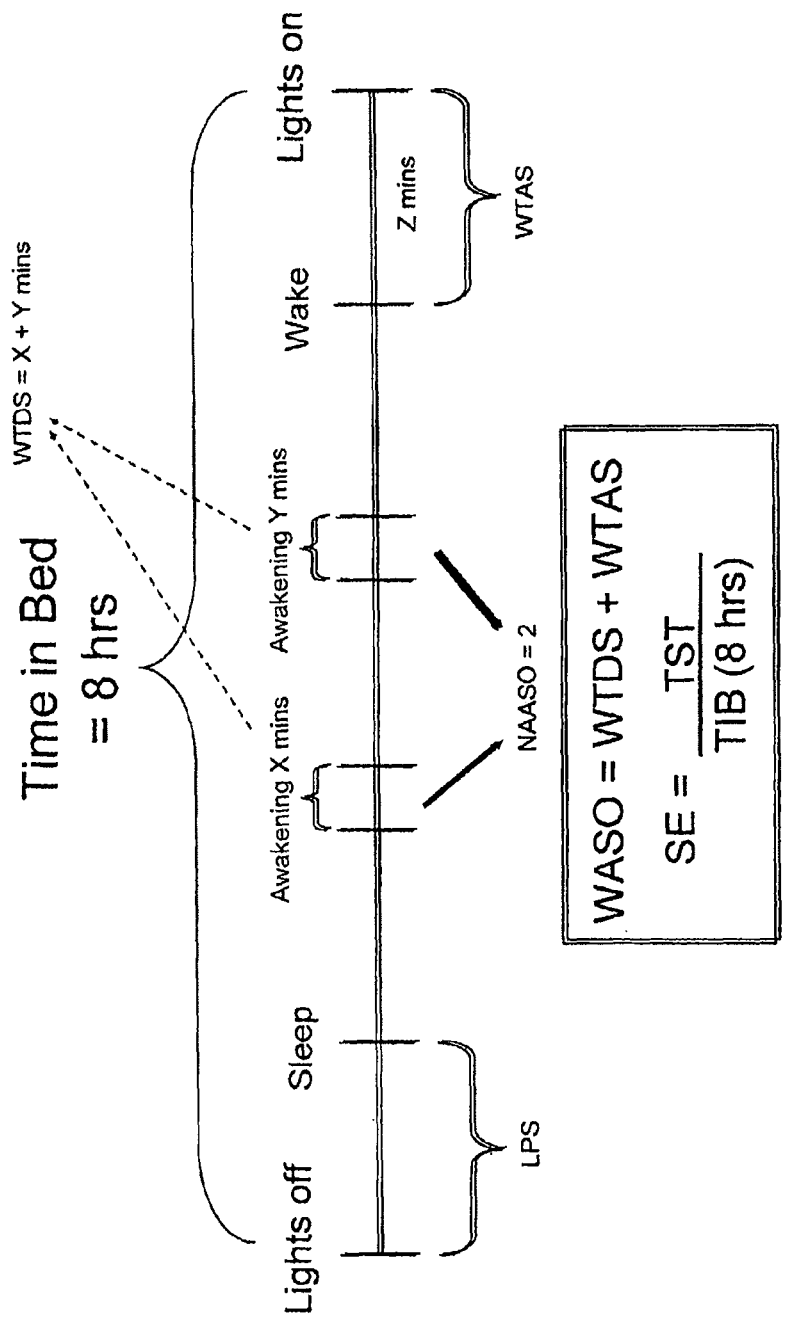
FIG. 1 illustrates the different parameters that can be analyzed using polysomnography.

Many individuals currently suffer from sleep disorders, such as insomnia. Some of these individuals with insomnia are subject to shorter total sleep periods due to premature final awakenings. Also, some of these individuals suffer from transient awakenings, particularly during the last 1-2 hours of their sleep period. The premature final awakenings and the transient awakening during the final hours of sleep causes the individuals to be tired and un-refreshed, and can decrease their overall well-being and productivity. Thus, there is a need for methods of treating such individuals to improve sleep efficiency and the total sleep time.

The present invention relates to methods of using doxepin, for example, low doses of doxepin to improve the sleep of such individuals. Some embodiments relate to methods of using doxepin to prevent or reduce the early final awakening of an individual. Also, some embodiments relate to decreasing the transient awakenings during the last hours of sleep, preferably in the last hour of a sleep period for an individual.

As mentioned above, various medications are currently approved for the treatment of sleep disorders, such as insomnia. Many of the approved medications have unfavorable side effects. Additionally, the previously approved medications do not effectively manage the sleep experience for an individual taking the medication. For example, the approved medications do not improve fragmented sleep for a patient in the final hours of sleep, especially the last hour of a sleep period. Furthermore, as an example, many of the already approved medications do not reduce or prevent the early final awakening of an individual that is taking the medication. In short, the currently approved medications do not completely improve the sleep experience for patients in the final hours of sleep.

Doxepin HCl is a tricyclic compound currently approved for treatment of depression. The recommended daily dose for the treatment of depression ranges from 75 mg to 300 mg. Doxepin, unlike most FDA approved products for the treatment of insomnia, is not a Schedule IV controlled substance. U.S. Pat. Nos. 5,502,047 and 6,211,229, the entire contents of which are incorporated herein by reference, describe the use of doxepin for the treatment chronic and non-chronic (e.g., transient/short term) insomnias at dosages far below those used to treat depression.

Some embodiments of this invention relate to the ability of low-dose doxepin, pharmaceutically acceptable salts or prodrugs thereof to prevent premature or early final awakenings, and/or to improve fragmented sleep, which can be measured by decrements in sleep efficiency (SE) during the seventh and eighth hours of an eight hour period of sleep, by identifying an individual in need of such treatment, and providing a low dose of doxepin, a pharmaceutically acceptable salt thereof, or a prodrug thereof to the individual.

Definitions

As used herein, the term "polysomnography" (PSG) refers a diagnostic test during which a number of physiologic variables are measured and recorded during sleep. Physiologic sensor leads are placed on the patient in order to record brain electrical activity, eye and jaw muscle movement, leg muscle movement, airflow, respiratory effort (chest and abdominal excursion), EKG and oxygen saturation Information is gathered from all leads and fed into a computer and outputted as a series of waveform tracings which enable the technician to visualize the various waveforms, assign a score for the test, and assist in the diagnostic process. The primary efficacy variable, wake time during sleep (WTDS) and various secondary efficacy variables are all based on the PSG and are defined as follows.

"Wake Time During Sleep" (WTDS), typically expressed in minutes, is the number of wake events (epochs) after the onset of persistent sleep and prior to final awakening, divided by two. Each epoch is defined as a 30-second duration on the PSG recording.

"Wake Time After Sleep" (WTAS), typically expressed in minutes, is the number of epochs after the final awakening until the end of PSG recording (i.e., a wake epoch immediately prior to the end of the recording), divided by two. If the patient does not have a wake epoch immediately prior to the end of the recording, then WTAS is zero.

"Wake After Sleep Onset" (WASO) is the sum of WTDS and WTAS.

"Latency to Persistent Sleep" (LPS), typically expressed in minutes, is the number of epochs from the beginning of the PSG recording (lights-out) to the start of the first 20 consecutive non-wake epochs, divided by two.

"Total Sleep Time" (TST), typically expressed in minutes, is the number of non-wake epochs from the beginning of the PSG recording to the end of the recording, divided by two.

"Sleep Efficiency" (SE) is the TST divided by the time in bed (8 hours), multiplied by 100 and expressed as a percentage. This also can be divided into SE for each third-of-the-night of sleep, reflecting the SE for each 160 minute time interval across the night. Finally, SE can be measured for individual hours during the night or sleep period, for example the final hour of the sleep period.

The term "fragmented sleep" can refer to interrupted sleep over a measurement period or sleep period, for example the time a patient is awake during period of measurement. Fragmentation can occur as a result of multiple awakenings or one or more awakenings of a long duration.

The term "prodrug" refers to an agent that is converted into the active drug in vivo. Prodrugs are often useful because, in some situations, they may be easier to administer than the active drug. They may, for instance, be bioavailable by oral administration whereas the active drug is not. The prodrug may also have improved solubility in pharmaceutical compositions over the active drug. An example, without limitation, of a prodrug would be a compound of the present invention which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety.

The term "pharmaceutically acceptable salt" refers to an ionic form of a compound that does not cause significant irritation to an organism to which it is administered and does not abrogate the biological activity and properties of the compound. Pharmaceutical salts can be obtained by reacting a compound of the invention with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutical salts can also be obtained by reacting a compound of the invention with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glutamine, tris(hydroxymethyl)methylamine, and salts with amino acids such as arginine, lysine, and the like.

The term "low dose" can refer to a daily dose range of between about 0.5 and 6 mg. In some embodiments, daily dosages of low dose doxepin can be about 1, 2, 3, 4, 5 or 6 mg. These dosages have reduced side effects, are surprisingly effective, and have a relatively rapid onset. In one embodiment, an initial daily dosage of about 1 mg can be given. If the desired improvement in sleep is not achieved, then the dosage may be incrementally increased until the desired dosage is achieved or until a maximum desired dosage is reached which can be, for example, 2 mg, 3 mg, 4 mg, 5 mg or 6 mg. It should be noted that other dosages of doxepin can be used in the embodiments described herein. For example, the dosage can be about 0.5 to about 10 mg.

Compounds

Doxepin:

Doxepin HCl is a tricyclic compound currently approved and available for treatment of depression and anxiety. Doxepin has the following structure:

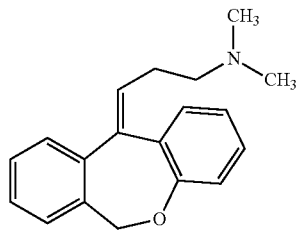 [SMILES: CN(C)CC/C=C1/c2ccccc2COc2ccccc21]

For all compounds disclosed herein, unless otherwise indicated, where a carbon-carbon double bond is depicted, both the cis and trans stereoisomers, as well as mixtures thereof are encompassed.

Doxepin belongs to a class of psychotherapeutic agents known as dibenzoxepin tricyclic compounds, and is currently approved and prescribed for use as an antidepressant to treat depression and anxiety. Doxepin has a well-established safety profile, having been prescribed for over 35 years.

Doxepin, unlike most FDA approved products for the treatment of insomnia, is not a Schedule IV controlled substance. U.S. Pat. Nos. 5,502,047 and 6,211,229, the entire contents of which are incorporated herein by reference, describe the use of doxepin for the treatment chronic and non-chronic (e.g., transient/short term) insomnias at dosages far below those used to treat depression.

It is contemplated that doxepin for use in the methods described herein can be obtained from any suitable source or made by any suitable method. As mentioned, doxepin is approved and available in higher doses (75-300 milligrams) for the treatment of depression and anxiety. Doxepin HCl is available commercially and may be obtained in capsule form from a number of sources. Doxepin is marketed under the commercial name SINEQUAN® and in generic form, and can be obtained in the United States generally from pharmacies in capsule form in amounts of 10, 25, 50, 75, 100 and 150 mg dosage, and in liquid concentrate form at 10 mg/mL. Doxepin HCl can be obtained from Plantex Ltd. Chemical Industries (Hakadar Street, Industrial Zone, P.O. Box 160, Netanya 42101, Israel), Sifavitor S.p.A. (Via Livelli 1-Frazione, Mairano, Italy), or from Dipharma S.p.A. (20021 Baranzate di Bollate, Milano, Italy). Also, doxepin is commercially available from PharmacyRx (NZ) (2820 1$^{st}$ Avenue, Castlegar, B.C., Canada) in capsule form in amounts of 10, 25, 50, 75, 100 and 150 mg. Furthermore, Doxepin HCl is available in capsule form in amounts of 10, 25, 50, 75, 100 and 150 mg and in a 10 mg/ml liquid concentrate from CVS Online Pharmacy Store (CVS.com).

Also, doxepin can be prepared according to the method described in U.S. Pat. No. 3,438,981, which is incorporated herein by reference in its entirety. It should be noted and understood that although many of the embodiments described herein specifically refer to "doxepin," other doxepin-related compounds can also be used, including, for example, pharmaceutically acceptable salts, prodrugs, metabolites, in-situ salts of doxepin formed after administration, and solid state forms, including polymorphs and hydrates.

Metabolites:

In addition, doxepin metabolites can be prepared and used. By way of illustration, some examples of metabolites of doxepin can include, but are not limited to, desmethyldoxepin, hydroxydoxepin, hydroxyl-N-desmethyldoxepin, doxepin N-oxide, N-acetyl-N-desmethyldoxepin, N-desmethyl-N-formyldoxepin, quaternary ammonium-linked glucuronide, 2-O-glucuronyldoxepin, didesmethyldoxepin, 3-O-glucuronyldoxepin, or N-acetyldidesmethyldoxepin. The metabolites of doxepin can be obtained or made by any suitable method, including the methods described above for doxepin.

Desmethyldoxepin has the following structure:

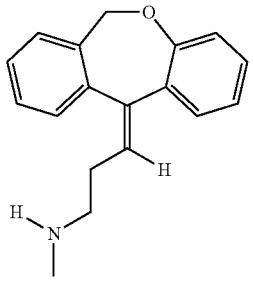 [SMILES: CNCC/C=C1\c2ccccc2COc2ccccc21]

Desmethyldoxepin is commercially available as a forensic standard. For example, it can be obtained from Cambridge Isotope Laboratories, Inc. (50 Frontage Road, Andover, MA). Desmethyldoxepin for use in the methods discussed herein can be prepared by any suitable procedure. For example, desmethyldoxepin can be prepared from 3-methylaminopropyl triphenylphosphonium bromide hydrobromide and 6,11-dihydrodibenz(b,e)oxepin-11-one according to the method taught in U.S. Pat. No. 3,509,175, which is incorporated herein by reference in its entirety.

Hydroxydoxepin has the following structure:

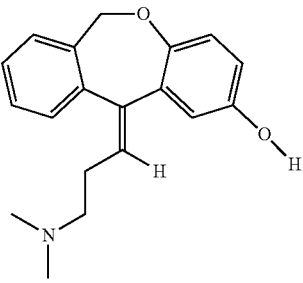 [SMILES: CN(C)CC/C=C1\c2ccccc2COc2ccc(O)cc21]

2-Hydroxydoxepin can be prepared by any suitable method, including as taught by Shu et al. (*Drug Metabolism and Disposition* (1990) 18:735-741), which is incorporated herein by reference in its entirety.

Hydroxyl-N-desmethyldoxepin has the following structure:

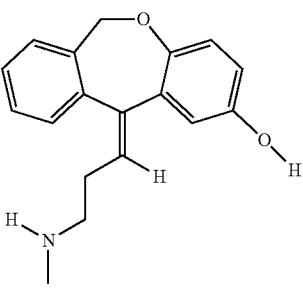 [SMILES: CNCC/C=C1\c2ccccc2COc2ccc(O)cc21]

2-Hydroxy-N-desmethyldoxepin can be prepared any suitable method.

Doxepin N-oxide has the following structure:

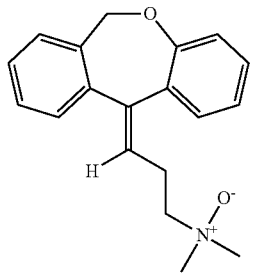 [SMILES: C[N+](C)([O-])CC/C=C1/c2ccccc2COc2ccccc21]

Doxepin N-oxide can be prepared by any suitable method. For example, doxepin N-oxide can be prepared as taught by Hobbs (*Biochem Pharmacol* (1969) 18:1941-1954), which is hereby incorporated by reference in its entirety.

N-acetyl-N-desmethyldoxepin has the following structure:

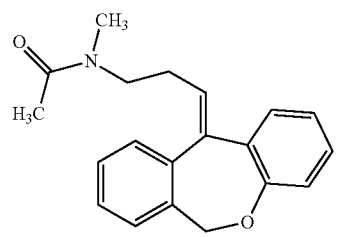 [SMILES: CC(=O)N(C)CC/C=C1\c2ccccc2COc2ccccc21]

N-acetyl-N-desmethyldoxepin can be prepared by any suitable means. For example, (E)-N-acetyl-N-desmethyldoxepin has been produced in filamentous fungus incubated with doxepin as taught by Moody et al. (*Drug Metabolism and Disposition* (1999) 27:1157-1164), hereby incorporated by reference in its entirety.

N-desmethyl-N-formyldoxepin has the following structure:

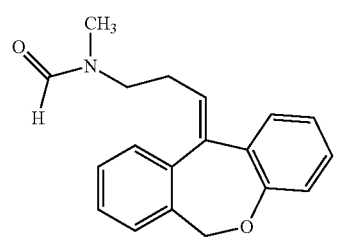 [SMILES: CN(C=O)CC/C=C1\c2ccccc2COc2ccccc21]

N-desmethyl-N-formyldoxepin can be prepared by any suitable means. For example, (E)-N-desmethyl-N-formyldoxepin has been produced in filamentous fungus incubated with doxepin as taught by Moody et al. (*Drug Metabolism and Disposition* (1999) 27:1157-1164), hereby incorporated by reference in its entirety.

N-acetyldidesmethyldoxepin has the following structure:

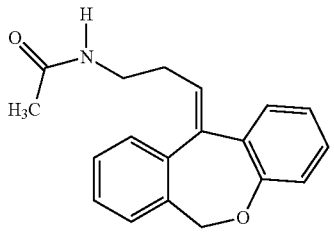 [SMILES: CC(=O)NCC/C=C1\c2ccccc2COc2ccccc21]

N-acetyldidesmethyldoxepin can be prepared by any suitable means. For example, (E)-N-acetyldidesmethyldoxepin has been produced in filamentous fungus incubated with doxepin as taught by Moody et al. (Drug Metabolism and Disposition (1999) 27:1157-1164), hereby incorporated by reference in its entirety.

Didesmethyldoxepin has the following structure:

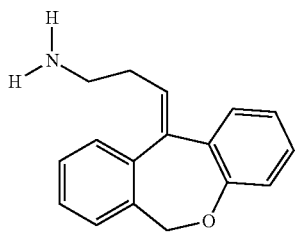 [SMILES: NCC/C=C1\c2ccccc2COc2ccccc21]

Didesmethyldoxepin can be prepared by any suitable means. For example, (Z)- and (E)-didesmethyldoxepin have been isolated from plasma and cerebrospinal fluid of depressed patients taking doxepin, as taught by Deuschle et al. (Psychopharmacology (1997) 131:19-22), hereby incorporated by reference in its entirety.

3-O-glucuronyldoxepin has the following structure:

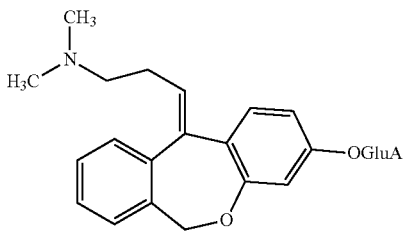

3-O-glucuronyldoxepin can be prepared by any suitable means. For example, (E)-3-O-glucuronyldoxepin has been isolated from the bile of rats given doxepin, as described by Shu et al. (Drug Metabolism and Disposition (1990)18: 1096-1099), hereby incorporated by reference in its entirety.

2-O-glucuronyldoxepin has the following structure:

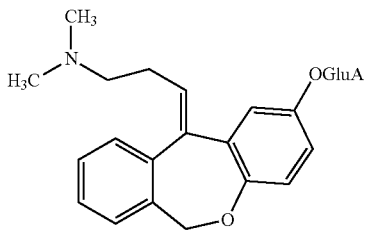

2-O-glucuronyldoxepin can be prepared by any suitable means. For example, (E)-2-O-glucuronyldoxepin has been isolated from the bile of rats given doxepin, and also in the urine of humans given doxepin, as described by Shu et al. (Drug Metabolism and Disposition (1990) 18:1096-1099), hereby incorporated by reference in its entirety.

Quaternary ammonium-linked glucuronide of doxepin (doxepin $N^+$-glucuronide) has the following structure:

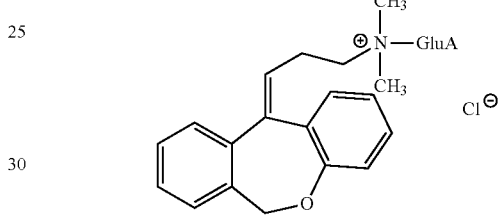

$N^+$-glucuronide can be obtained by any suitable means. For example, doxepin $N^+$-glucuronide can be prepared as taught by Luo et al. (Drug Metabolism and Disposition, (1991) 19:722-724), hereby incorporated by reference in its entirety.

Pharmaceutically Acceptable Salts:

As mentioned above, the methods and other embodiments described herein can utilize any suitable pharmaceutically acceptable salt or prodrug of doxepin, or salts or prodrugs of doxepin metabolites. Therefore, the substitution or use in combination of salts and prodrugs is specifically contemplated in the embodiments described herein. The pharmaceutically acceptable salts and prodrugs can be made by any suitable method.

The term "pharmaceutically acceptable salt" refers to an ionic form of a compound that does not cause significant irritation to an organism to which it is administered and does not abrogate the biological activity and properties of the compound. Pharmaceutical salts can be obtained by reacting a compound of the invention with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutical salts can also be obtained by reacting a compound of the invention with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glutamine, tris(hydroxymethyl)methylamine, and salts with amino acids such as arginine, lysine, and the like. Pharmaceutically acceptable salts are more fully described in the following paragraph.

The acids that can be used to prepare pharmaceutically acceptable acid addition salts include, for example, those that form non-toxic acid addition salts, i.e., salts containing pharmacologically acceptable anions, such as the acetate, benzenesulfonate, benzoate, bicarbonate, bisulfate, bitartrate, borate, bromide, calcium edetate, camsylate, carbonate, chloride, clavulanate, citrate, dihydrochloride, edetate, dislyate, estolate, esylate, ethylsuccinate, fumarate, gluceptate, gluconate, glutamate, glycollylarsanilate, hexylresorcinate, hydrabamine, hydrobromide, hydrochloride, iodide, isothionate, lactate, lactobionate, laurate, malate, maleate, mandelate, mesylate, methylsulfate, mucate, napsylate, nitrate, oleate, oxalate, pamoate (embonate), palmitate, pantothenate, phospate/diphosphate, polygalacturonate, salicylate, stearate, subacetate, succinate, tannate, tartrate, teoclate, tosylate, triethiodode, and valerate salts.

The bases that can be used to prepare pharmaceutically acceptable base addition salts include, for example, those that form non-toxic base addition salts, i.e., base salts formed with metals or amines, such as alkali and alkaline earth metals or organic amines. Non-limiting examples of metals used as cations include sodium, potassium, magnesium, calcium, and the like. Also included are heavy metal salts such as for example silver, zinc, cobalt, and cerium. Non-limiting examples of suitable amines include N,N'-dibenzylethylenediamine, chloroprocaine, choline, diethanolamine, ethylenediamene, N-methylglucamine, and procaine.

Prodrugs:

The term "prodrug" refers to an agent that is converted into the active drug in vivo. Prodrugs are often useful because, in some situations, they can be easier to administer than the active drug. They can, for instance, be bioavailable by oral administration whereas the active drug is not. The prodrug may also have improved solubility in pharmaceutical compositions over the active drug. An example, without limitation, of a prodrug would be a compound of the present invention which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. Examples of prodrug groups can be found in, for example, T. Higuchi and V. Stella, in "Pro-drugs as Novel Delivery Systems," Vol. 14, A.C.S. Symposium Series, American Chemical Society (1975); H. Bundgaard, "Design of Prodrugs," Elsevier Science, 1985; and "Bioreversible Carriers in Drug Design: Theory and Application," edited by E. B. Roche, Pergamon Press: New York, 14-21 (1987), each of which is hereby incorporated by reference in its entirety.

Methods of Using Low Dose Doxepin

Some embodiments relate to methods for reducing or preventing premature awakening in a patient in need thereof. The methods can include the step of identifying a patient having a sleep disorder in which, for a given sleep period of desired sleep, for example an 8 hour period, the patient experiences a sleep period that terminates prior to or during the final 60 minutes of the period; and administering to the patient a dosage of doxepin that is effective to lengthen the sleep period, preferably between about 1 and 6 mg. In some aspects the patient can experience a sleep period that terminates within the final 60 minutes, 45 minutes, 30 minutes or 15 minutes. In other aspects the sleep period can terminate even earlier, for example, during the final 90 minutes, the final 120 minutes, or longer. In some aspects, the sleep period may be lengthened by administering low dose doxepin to extend the sleep period to terminate during or after hour 7 (e.g., hour 7.5) of an 8 hour period of sleep. Also, the patients can be identified as being in need of reduced wake time during (or after) sleep.

Further, some embodiments relate to methods for improving fragmented sleep in the final hours of a sleep period for a patient, preferably during the final hour or the $8^{th}$ hour of sleep. The methods can include, for example, the steps of identifying a patient suffering from or experiencing fragmented sleep during last hour or hours of a sleep period, and administering to the patient doxepin in a dosage between about 1 mg and 6 mg. Preferably, the methods can be used to reduce or improve fragmented sleep during the 8th hour of a sleep period. In some aspects the dosage of doxepin can be about 1 mg, 3 mg or 6 mg.

Some embodiments relate to methods of using low dose doxepin to decrease WTAS in an individual who is prone to early awakenings. An individual with such a need can be identified, and low doses of doxepin can be administered to the individual, for example, prior to the sleep period.

The methods described herein can be used to treat individuals suffering from a sleep disorder, such as insomnia. The individual can suffer from a chronic insomnia or a non-chronic insomnia. For chronic (e.g., greater than 3-4 weeks) or non-chronic insomnias, a patient may suffer from difficulties in sleep onset, sleep maintenance (interruption of sleep during the night by periods of wakefulness), sleep duration, sleep efficiency, premature early-morning awakening, or a combination thereof. Also, the insomnia may be attributable to the concurrent use of other medication, for example. The non-chronic insomnia can be, for example, a short term insomnia or a transient insomnia. The chronic or non-chronic insomnia can be a primary insomnia or an insomnia that is secondary or attributable to another condition, for example a disease such as depression or chronic fatigue syndrome. In some aspects, the patient can be one that is not suffering from an insomnia that is a component of a disease, or a patient can be treated that is otherwise healthy. As previously mentioned, the chronic or non-chronic insomnia can be a primary insomnia, that is, one that is not attributable to another mental disorder, a general medical condition, or a substance. In many cases, such conditions may be associated with a chronic insomnia and can include, but are not limited to, insomnia attributable to a diagnosable DSM-IV disorder, a disorder such as anxiety or depression, or a disturbance of the physiological sleep-wake system. In some aspects the insomnia can be non-chronic, or of short duration (e.g., less than 3-4 weeks). Examples of causes of such insomnia may be extrinsic or intrinsic and include, but are not limited to environmental sleep disorders as defined by the International Classification of Sleep Disorders (ICSD) such as inadequate sleep hygiene, altitude insomnia or adjustment sleep disorder (e.g., bereavement). Also, short-term insomnia may also be caused by disturbances such as shift-work sleep disorder.

Administration of Doxepin

In performing the methods, doxepin, a pharmaceutically acceptable salt of doxepin, or prodrug of doxepin can be administered using any suitable route or method of delivery. Also, doxepin, a pharmaceutically acceptable salt or a prodrug thereof can be included and administered in a composition.

Suitable routes of administration include oral, buccal, sublingual, transdermal, rectal, topical, transmucosal, or intestinal administration; parenteral delivery, including intramuscular, subcutaneous, intravenous, intramedullary injections, as well as intrathecal, direct intraventricular, intraperitoneal, intranasal, or intraocular injections.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Administration though oral pathways can be accomplished, for example, using a capsule, a tablet, a granule, a spray, a syrup, a liquid, powder, granules, pastes (e.g., for application to the tongue). Oral administration can be accomplished using fast-melt formulations, for example. Pharmaceutical preparations for oral use can be obtained by mixing one or more solid excipient with pharmaceutical combination of the invention, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Pharmaceutical preparations which can be used orally, including sublingually, include for example, liquid solutions, powders, and suspensions in bulk or unit dosage forms. Also, the oral formulations can include, for example, pills, tablets, granules, sprays, syrups, pastes, powders, boluses, pre-measured ampules or syringes, push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take any suitable form, for example, tablets or lozenges.

For topical administration, the compounds may be formulated for administration to the epidermis as ointments, gels, creams, pastes, salves, gels, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition, any of the compounds and compositions described herein can also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt. Furthermore, any of the compounds and compositions described herein also can be formulated as a fast-melt preparation. The compounds and compositions can also be formulated and administered as a drip, a suppository, a salve, an ointment, an absorbable material such a transdermal patch, or the like.

One can also administer the compounds of the invention in sustained release forms or from sustained release drug delivery systems. A description of representative sustained release materials can be found in the incorporated materials in Remington: The Science and Practice of Pharmacy ($20^{th}$ ed, Lippincott Williams & Wilkens Publishers (2003)), which is incorporated herein by reference in its entirety.

A variety of techniques for formulation and administration can be found in Remington: The Science and Practice of Pharmacy ($20^{th}$ ed, Lippincott Williams & Wilkens Publishers (2003)), which is incorporated herein by reference in its entirety.

Compositions

As mentioned above, doxepin, pharmaceutically acceptable salts, and/or prodrugs of the same can be used alone or in combination with other substances, such as for example, other insomnia or sleep medications, or with other medications that treat a primary illness. The doxepin alone or in combination can be included as part of a composition. The compounds and compositions can include any suitable form of the compound for pharmaceutical delivery, as discussed in further detail herein.

The compositions and formulations disclosed herein also can include one or more pharmaceutically acceptable carrier materials or excipients. Such compositions can be prepared for storage and for subsequent administration. Acceptable carriers or diluents for therapeutic use are well known in the pharmaceutical art, and are described, for example, in the incorporated material of *Remington: The Science and Practice of Pharmacy* (20th ed, Lippincott Williams & Wilkens Publishers (2003)), which is incorporated herein by reference in its entirety. The term "carrier" material or "excipient" herein can mean any substance, not itself a therapeutic agent, used as a carrier and/or diluent and/or adjuvant, or vehicle for delivery of a therapeutic agent to a subject or added to a pharmaceutical composition to improve its handling or storage properties or to permit or facilitate formation of a dose unit of the composition into a discrete article such as a capsule or tablet suitable for oral administration. Excipients can include, by way of illustration and not limitation, diluents, disintegrants, binding agents, adhesives, wetting agents, polymers, lubricants, glidants, substances added to mask or counteract a disagreeable taste or odor, flavors, dyes, fragrances, and substances added to improve appearance of the composition. Acceptable excipients include lactose, sucrose, starch powder, maize starch or derivatives thereof, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinyl-pyrrolidone, and/or polyvinyl alcohol, saline, dextrose, mannitol, lactose, lecithin, albumin, sodium glutamate, cysteine hydrochloride, and the like. Examples of suitable excipients for soft gelatin capsules include vegetable oils, waxes, fats, semisolid and liquid polyols. Suitable excipients for the preparation of solutions and syrups include, without limitation, water, polyols, sucrose, invert sugar and glucose. Suitable excipients for injectable solutions include, without limitation, water, alcohols, polyols, glycerol, and vegetable oils. The pharmaceutical compositions can additionally include preservatives, solubilizers, stabilizers, wetting agents, emulsifiers, sweeteners, colorants, flavorings, buffers, coating agents, or antioxidants. Sterile compositions for injection can be formulated according to conventional pharmaceutical practice as described in the incorporated material in *Remington: The Science and Practice of Pharmacy* (20th ed, Lippincott Williams & Wilkens Publishers (2003)). For example, dissolution or suspension of the active compound in a vehicle such as water or naturally occurring vegetable oil like sesame, peanut, or cottonseed oil or a synthetic fatty vehicle like ethyl oleate or the like may be desired. Buffers, preservatives, antioxidants and the like can be incorporated according to accepted pharmaceutical practice. The compound can also be made in microencapsulated form. In addition, if desired, the injectable pharmaceutical compositions may contain minor amounts of nontoxic auxiliary substances, such as wetting agents, pH buffering agents, and the like. If desired, absorption enhancing preparations (for example, liposomes), can be utilized.

The compositions and formulations can include any other agents that provide improved transfer, delivery, tolerance, and the like. These compositions and formulations can include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." *Regul. Toxicol. Pharmacol.* 32(2):210-8 (2000), Charman WN "Lipids, lipophilic drugs, and oral drug delivery—some emerging concepts." *J Pharm Sci* 0.89(8):967-78 (2000), Powell et al. "Compendium of excipients for parenteral formulations" *PDA J Pharm Sci Technol.* 52:238-311 (1998) and the citations therein for additional information related to formulations, excipients and carriers well known to pharmaceutical chemists.

One can also administer the compounds of the invention in sustained release forms or from sustained release drug delivery systems. A description of representative sustained release materials can be found in the incorporated materials in *Remington: The Science and Practice of Pharmacy* (20th ed, Lippincott Williams & Wilkens Publishers (2003)).

Dosage

As mentioned above, in some embodiments the preferable dosage can be between about 1 mg and 6 mg. Preferably, the dosage can be about 0.5 mg, 1 mg, about 2 mg, about 3 mg, about 4 mg, about 5 mg or about 6 mg. It should be noted that in some embodiments the dosage can be between about 0.01 mg and 20 mg or between about 0.5 mg and 10 mg. Further, the dosage can be about 7 mg, about 8 mg, about 9 mg, or about 10 mg.

The selected dosage level can depend upon, for example, the route of administration, the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved. It will be understood, however, that the specific dose level for any particular patient can depend upon a variety of factors including the genetic makeup, body weight, general health, diet, time and route of administration, combination with other drugs and the particular condition being treated, and its severity. For the treatment of insomnia, preferably one dose is administered prior to bedtime.

Figure 2:
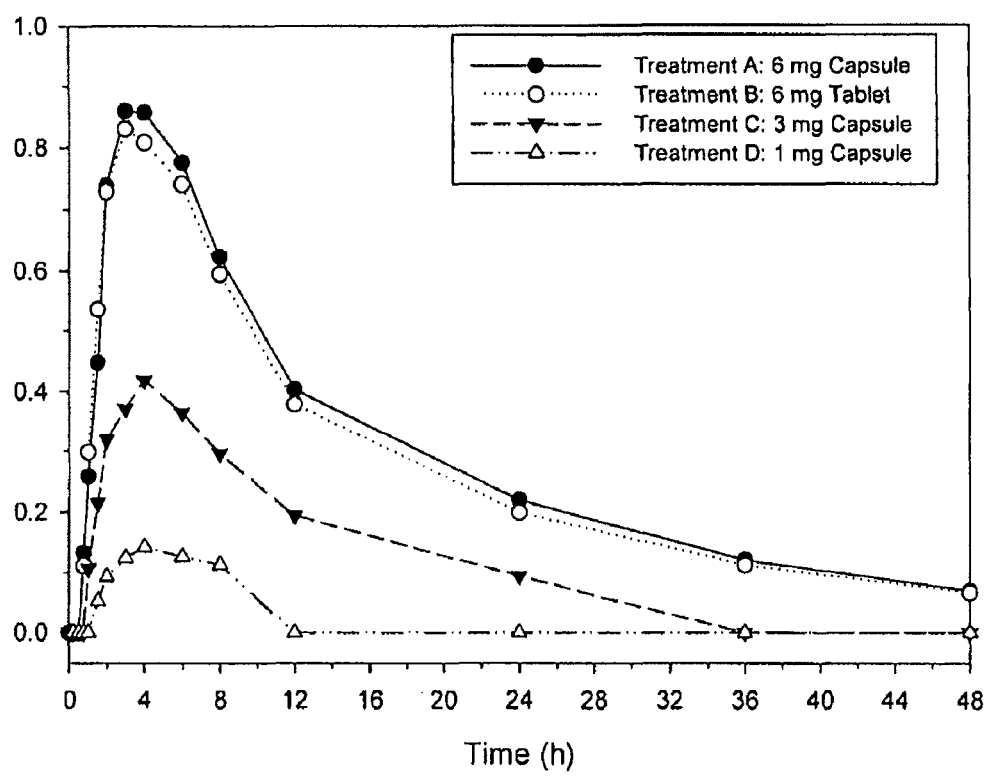
FIG. 2 is a graph showing the doxepin plasma profile concentration at various time points for 1 mg, 3 mg and 6 mg doxepin.

The selected dosage can also be determined by targeting a mean plasma concentration profile that has been associated with improvement in one or more PSG sleep variables including LPS, WASO, TST, SE, WTDS, or WTAS (FIG. 1). Examples of such plasma concentration profiles are shown in FIG. 2. The target plasma concentration profile may be achieved by any suitable route of administration including oral, buccal, sublingual, transdermal, rectal, topical, transmucosal, or intestinal administration; parenteral delivery, including intramuscular, subcutaneous, intravenous, intramedullary injections, as well as intrathecal, direct intraventricular, intraperitoneal, intranasal, or intraocular injections using any suitable formulation.

EXAMPLES

Example 1

Doxepin is prepared by the following method.

(a) A Grignard compound is prepared in the conventional manner from 4.8 g (0.2 gram-atom) magnesium in 100 mL ether and 30 g (34 ml) (3-chloropropyl)-tertbutyl ether and 16.40 grams (0.078 mol) 6,11-dihydrodibenzo-[b,e]-oxepine-11-one dissolved in 100 mL ether is added in dropwise fashion so that the contents of the flask boil lightly. The mixture is heated for 1 hour with agitation in a reflux condenser to complete the reaction and then it is decomposed with ammonium chloride solution. The product which is obtained by separating, drying and eliminating the solvent produced, when the ether residue (24.0 g) is extracted with ligroin, amounts to 20.3 g (80.0% of theory) of 11-(3-tertbutoxypropyl)-11-hydroxy-6,11-dihydrodibenzo-[b,e]-oxepine, having a melting point of 124-126° C. The (3-chloropropyl)-tertbutyl ether is thereafter obtained in the following manner: 19 g (0.2 mol) 1-chloropropanol-(3), 50 mL liquid isobutylene and 0.5 mL concentrated sulfuric acid are permitted to stand for 24 hours in an autoclave, then are poured into excess sodium bicarbonate solution and extracted with ether. The ether solution is dried with calcium chloride and distilled. 23.6 grams of (3-chloropropyl)-tert-butyl ether having a boiling point of 150-156° C. (78% of theory) are recovered.

(b) 30.8 grams of the 11-(3-tertbutoxypropyl)-11-hydroxy-6,11-dihydrodibenzo-[b,e]-oxepine obtained according to (a) above and 150 ml absolute alcoholic hydrochloric acid are heated for 1 hour at ebullition. After removing the solvent by evaporation, the residue is crystallized with ligroin, 21.0 grams (88.5% of theory) of 11-(3-hydroxypropylidene)-6,11-dihydrodibenzo-[b,e]-oxepine having a melting point of 108-111° C. were obtained. After recrystallization from acetic acid ester, the compound melts at 112-114° C.

(c) 5.0 ml thionyl chloride dissolved in 5 mL benzene is added dropwise at room temperature to 12.6 g (0.05 mol) of the 11-(3-hydroxypropylidene)-6,11-dihydrodibenzo-[b,e]-oxepine obtained in part (b) above. After 1 hour of standing, the contents of the flask are heated at ebullition for 2 hours. The volatile components are thereafter removed and the remainder distilled using high vacuum. The yield amounts to 10.6 g (78.5% of theory) of 11-(3-chloropropylidene)-6,11-dihydrodibenzo-[b,e]-oxepine having a B.P.0.1 169-172° C., a melting point of 106-111° C. After recrystallization from 20 ml of acetic acid ester, 9.1 g (67.5% of theory) of pure product having a melting point of 113-115° C. is obtained. The crude product can however be used quite easily for further processing.

(d) 5.4 g (0.02 mol) of the 11-(3-chloropropylidene)-6,11-dihydrodibenzo-[b,e]-oxepine, prepared according to (c) above, in 20 mL tetrahydrofuran and 5.5 g (0.12 mol) dimethylamine in 20 mL ethanol is heated together for 3 hours using a glass autoclave and a temperature of 95-100° C. (boiling water bath). Water and 6 N hydrochloric acid are added to the contents of the autoclave and the mixture is extracted with ether. The separated, aqueous-acid components are then made alkaline with dilute caustic soda solution, and the oil thereby separated is taken up in ether. The ether residue, after distillation in a high vacuum, produces 4.1 g (73.5% of theory) of 11-(3-dimethylamino-propylidene)-6,11-dihydrodibenzo-[b,e]-oxepine, having a B.P.$_{0.1}$ 147-150° C. The melting point of the hydrochloride is 182-184° C. (recrystallized from isopropanol).

Example 2

Preparation of Desmethyldoxepin

Desmethyldoxepin is prepared according to the following method. Anhydrous 3-methylaminopropyltriphenylphosphonium bromide hydrobromide (1530 g) prepared as in U.S. Pat. No. 3,509,175, is suspended in 4.5 L dry tetrahydrofuran and 6.0 moles of butyl lithium in heptane is added during 1 hour. After an additional 30 minutes, 483 g of 6,11-dihydrodibenz[b,e]oxepin-11-one, is added to the deep red solution and the reaction is maintained at reflux for 10 hours. Water, 500 mL, is added at room temperature and the solvent is removed in vacuo. The crude residue is treated with 10% hydrochloric acid until acidic (pH 2) and then 1.5 L benzene is added. After stiffing, the mixture separates into three phases (an insoluble hydrochloride salt product phase, an aqueous phase and an organic phase). The benzene layer is removed by decantation and the remaining mixture is rendered basic with 10% sodium hydroxide solution and is extracted with 3×1500 mL portions of benzene. The benzene extracts are washed, then dried with anhydrous sodium sulfate and concentrated in a vacuum leaving a solid residue of desmethyldoxepin.

Example 3

Preparation of (E)-Desmethyldoxepin (E)-Desmethyldoxepin is prepared from doxepin hydrochloride as follows. Doxepin hydrochloride (E/Z=85/15) (55.0 g, 0.174 mol) is dissolved in 600 mL H2O, made basic with 6M NaOH, and extracted with CHCl3 (3×600 mL). The CHCl3 extracts are combined, dried over Na2SO4, and solvent removed in vacuo. The resulting oil is dissolved in 250 mL EtOH, then 21.15 g (0.182 mol) of maleic acid dissolved in 100 mL EtOH is added slowly, with stirring, followed by an additional 350 mL EtOH. The resulting cloudy solution is refluxed until it becomes clear, then allowed to stand overnight at room temperature; the resulting crystals are isolated by vacuum filtration. Additional recrystallization from EtOH yields a white crystalline product ((E)-Doxepin maleate) with an E/Z ratio of 98/2. (E)-Doxepin maleate (2.50 g, 6.32 mmol) is then partially dissolved in 60 mL H2O, made basic with 6M NaOH, and extracted with CHCl3 (3×60 mL). The CHCl3 extracts are combined, washed with 60 mL brine, dried over Na2SO4, and solvent removed in vacuo. The resulting oil is re-dissolved in 10 mL CHCl3, 1.8 mL (13 mmol) of triethylamine added, 1.8 mL (13 mmol) of 2,2,2-trichloroethyl-chloro-formate added, and reaction stirred under N2 for 3.5 hours. The completed reaction is then diluted with 140 mL Et2O, washed successively with 0.5M HCl (2×140 mL), H2O (140 mL), and brine (140 mL), then dried over MgO4 and solvent removed in vacuo. Resulting material is further purified by silica gel column chromatography, eluting with EtOAc/Hex (20/80), to afford 1.48 g (3.36 mmol) of the desired product as a clear oil. The N-protected (E)-desmethyldoxepin intermediate (1.44 g, 3.27 mmol) is then dissolved in 12 mL THF, 2.88 g of zinc powder added, 2.3 mL of 1M sodium phosphate (pH=5.5) added, and reaction stirred for 17 hours. The reaction mixture is then vacuum filtered, filtrate solvent removed in vacuo, and resulting residue purified by silica gel column chromatography, eluting with THF/MeOH/NH4OH (85/15/0.4), then THF/MeOH/NH4OH (75/25/0.4), to afford 744 mg (2.80 mmol) of the desired product as a pale yellow solid.

Example 4

Preparation of (Z)-Desmethyl Doxepin (Z)-Desmethyldoxepin is prepared from doxepin hydrochloride as follows. Doxepin hydrochloride (E/Z=85/15)

(100 g, 0.317 mol) is dissolved in 800 mL H2O, made basic with 6M NaOH, and extracted with CHCl3 (3×800 mL). The CHCl3 extracts are combined, dried over Na2SO4, and solvent removed in vacuo. The resulting oil is dissolved in 700 mL EtOH, then 36.7 g (0.317 mol) of maleic acid dissolved in 600 mL EtOH is added slowly, with stirring. The resulting cloudy solution is refluxed until clear, then allowed to stand overnight at room temperature. Crystals are isolated by vacuum filtration and the mother liquor saved. Crystals are recrystallized two additional times as above, and the three mother liquors saved and combined and solvent removed in vacuo. Recrystallization of mother liquor material from refluxing EtOH eventually affords 24 g of a mother liquor product which is 65% Z isomer in composition. Recrystallization of this material from 450 mL EtOH gives crystals (9.1 g) which are 80% Z isomer. This material is recrystallized from 170 mL CHCl3/CCl4 (50/50) at 4° C., yielding 7.65 g of crystalline material which is 87% Z isomer in composition. Three additional recrystallizations from CHCl3/CCl4 eventually affords 5.12 g (12.9 mmol) of the desired product ((Z)-Doxepin maleate) with an E/Z ratio of 4/96; melting point: 162-163° C. (Z)-Doxepin maleate (1.00 g, 2.53 mmol) is then partially dissolved in 35 mL H2O, made basic with 6M NaOH, and extracted with CHCl3 (3×35 mL). The CHCl3 extracts are combined, washed with 35 mL brine, dried over Na2SO4, and solvent removed in vacuo. The resulting oil is re-dissolved in 4 mL CHCl3, 0.65 mL (4.7 mmol) of triethylamine added, 0.65 mL (4.7 mmol) of 2,2,2-trichloroethyl-chloroformate added, and reaction stirred under N2 for 3.5 hours. The completed reaction is then diluted with 50 mL Et2O, washed successively with 0.5M HCl (2×50 mL), H2O (50 mL), and brine (50 mL), then dried over MgO4 and solvent removed in vacuo. Resulting material is further purified by silica gel column chromatography, eluting with EtOAc/Hex (20/80), to afford 710 mg (1.61 mmol) of the desired product as a clear oil. The N-protected (Z)-desmethyldoxepin (679 mg, 1.54 mmol) is then dissolved in 5.7 mL THF, 1.36 g of zinc powder added, 1.1 mL of 1M sodium phosphate (pH=5.5) added, and reaction stirred for 17 hours. The reaction mixture is then vacuum filtered, filtrate solvent removed in vacuo, and resulting residue purified by silica gel column chromatography, eluting with THF/MeOH/NH4OH (85/15/0.4), then THF/MeOH/NH4OH (82/18/0.4), to afford 364 mg (1.37 mmol) of the desired product as a pale yellow solid.

Example 5

Preparation of (Z)-2-Hydroxy-11-(3-dimethylamino-propylidene)-6,11-dihydrodibenzo[b,e]oxepin A mixture of 2-methoxy-11-(3-dimethylaminopropyl)-6,11-dihydrodibenzo[b,e]oxepin (165 mg, 0.005 mol) with glacial acetic acid (0.2 ml) and hydriodic acid (0.2 mL, 57%) was stirred and heated for 5 hr at 90° C. The product was then extracted and purified by pouring into ice water (25 mL), made alkaline with sodium hydroxide (2N) and extracted with ether (2×10 mL). The aqueous layer was then adjusted to pH 6.8 with hydrochloric acid (6N). The mixture was then brought to pH 7 by the addition of sodium bicarbonate solution (5%) and extracted with chloroform (2×10 mL). The extract was dried over anhydrous sodium sulfate and evaporated in vacuo to give a yellowish solid. The crude reaction product was purified by preparative TLC (chloroform/toluene/methanol/ammonia, 4:3:2:1, v/v).

Example 6

Preparation of (E)-2-Hydroxy-11-(3-dimethylamino-propylidene)-6,11-dihydrodibenzo[b,e]oxepin A mixture of (Z)-2-Hydroxy-11-(3-dimethylaminopropylidene)-6,11-dihydrodibenzo[b,e]oxepin (2.5 mg, $8.5 \times 10^{-6}$ mol) was dissolved in a mixture of hydrochloric acid (1 mL) and methanol (9 mL) and heated at 140° C. (oil bath) for 4 hr. The product was isolated by means of HPLC and evaporation of solvents.

Example 7

Preparation of (Z)-2-Hydroxy-11-(3-methylamino-propylidene)-6,11-dihydrodibenzo[b,e]oxepin A mixture of 2-methoxy-11-(3-methylaminopropyl)-6,11-dihydrodibenzo[b,e]oxepin (0.005 mol) with glacial acetic acid (0.2 ml) and hydriodic acid (0.2 ml, 57%) is stirred and heated for 5 hr at 90° C. The product is then extracted and purified by pouring into ice water (25 mL), made alkaline with sodium hydroxide (2N) and extracted with ether (2×10 mL). The aqueous layer is then adjusted to pH 6.8 with hydrochloric acid (6N). The mixture is then brought to pH 7 by the addition of sodium bicarbonate solution (5%) and extracted with chloroform (2×10 mL). The extract is dried over anhydrous sodium sulfate and evaporated in vacuo to give a yellowish solid. The crude reaction product is purified by preparative TLC (chloroform/toluene/methanol/ammonia, 4:3:2:1, v/v).

Example 8

Preparation of (E)-2-Hydroxy-11-(3-methylamino-propylidene)-6,11-dihydrodibenzo[b,e]oxepin A mixture of (Z)-2-Hydroxy-11-(3-methylaminopropylidene)-6,11-dihydrodibenzo[b,e]oxepin (2.5 mg) is dissolved in a mixture of hydrochloric acid (1 ml) and methanol (9 ml) and heated at 140° C. (oil bath) for 4 hr. The product is isolated by means of HPLC and evaporation of solvents.

Example 9

Preparation of Doxepin-N-Oxide

An aqueous solution of doxepin hydrochloride was made alkaline and extracted with methylene chloride. Solvent was removed and the residue, dissolved in methanol, was treated for 5 days with an excess of 30% hydrogen peroxide. Chromatographic examination indicated that the doxepin had been completely replaced by a more polar substance determined from its mass spectrum to be the N-oxide.

Hobbs, D. C., Distribution and Metabolism of Doxepin (1969) Biochem Pharmacol 18:1941-1954; which is incorporated herein by reference in its entirety.

Example 10

Preparation of (Z) Doxepin-N-Oxide

An aqueous solution of purified (Z)-doxepin hydrochloride is made alkaline and extracted with methylene chloride. Solvent is removed and the residue, dissolved in methanol, is treated for 5 days with an excess of 30% hydrogen peroxide. Chromatographic examination indicates that the doxepin has been completely replaced by a more polar substance determined from its mass spectrum to be the N-oxide of the (Z) isomer of doxepin.

Example 11

Preparation of (E)-Doxepin-N-Oxide

An aqueous solution of purified (E)-doxepin hydrochloride is made alkaline and extracted with methylene chloride. Solvent is removed and the residue, dissolved in methanol, is treated for 5 days with an excess of 30% hydrogen peroxide. Chromatographic examination indicates that the doxepin has been completely replaced by a more polar substance determined from its mass spectrum to be the N-oxide of the (E) isomer of doxepin.

Example 12

Isolation of (E)-N-acetyl-N-desmethyldoxepin, (E)-N-desmethyl-N-formyldoxepin, and (E)-N-acetyldidesmethyldoxepin (E)-N-acetyl-N-desmethyldoxepin, (E)-N-desmethyl-N-formyldoxepin, and (E)-N-acetyldidesmethyldoxepin are isolated from Cunninghamella elegans (C. elegans) as described in the incorporated materials of Moody et al. (Drug Metabolism and Disposition (1999) 27:1157-1164). Briefly, cultures of C. elegans ATCC 9245 are incubated for 48 h at 26° C. on a rotary shaker operating at 125 rpm and then 10 mg of doxepin hydrochloride (E./Z ratio 83:16%) dissolved in 0.5 ml sterile physiological saline solution are added. After 96 h of incubation, the contents of each flask, are filtered through glass wool into a separatory funnel and extracted with three equal volumes of ethyl acetate. The organic extracts are dried over sodium sulfate and evaporated to dryness in vacuo at 34°. The residue is dissolved in methanol and concentrated to approximately 100 μL by evaporation for analysis by HPLC.

The extract is injected repeatedly into a semipreparative scale HPLC system consisting of a Beckman model 100A pump, a Waters 486 turntable UV absorbance detector, and a Shimadzu model CR601 Chromatopac integrator. The compounds are eluted using a linear gradient of 30 to 75% methanol-buffer (v/v) over 30 min at 1.0 ml/min with a 10.0×250 mm column. The buffer used is 25 mM ammonium acetate, pH 7.2. Compounds with similar retention times are pooled. NMR and mass spectral analysis confirms the isolation of (E)-N-acetyl-N-desmethyldoxepin, (E)-N-desmethyl-N-formyldoxepin, and (E)-N-acetyldidesmethyldoxepin.

Example 13

Isolation of (Z)—N-acetyl-N-desmethyldoxepin, (Z)—N-desmethyl-N-formyldoxepin, and (Z)—N-acetyldidesmethyldoxepin (Z)—N-acetyl-N-desmethyldoxepin, (Z)—N-desmethyl-N-formyldoxepin, and (Z)—N-acetyldidesmethyldoxepin are isolated from Cunninghamella elegans (C. elegans) as described above in Example 12 for the (E) isomers. However, unlike Example 13, the cultures are initially incubated with doxepin enriched for the cis (Z)-isomer of doxepin at a Z/E ratio of greater than 85:15. NMR and mass spectral analysis confirms the isolation of (Z)—N-acetyl-N-desmethyldoxepin, (Z)—N-desmethyl-N-formyldoxepin, and (Z)—N-acetyldidesmethyldoxepin.

Example 14

Isolation of (E)- and (Z)—N-didesmethyldoxepin (E)- and (Z)—N-didesmethyldoxepin are isolated from blood serum and cerebrospinal fluid of patients treated with doxepin according to the methods described in the incorporated materials of Deuschle et al. (Psychopharmacology (1997) 131:19-22). Briefly, blood and cerebrospinal fluid are collected from patients being treated with doxepin. After centrifugation, (15000 g for 5 min), 100 μl of the samples is injected directly onto a clean-up column (10.0×4.0 mm) filled with Lichrospher RP-8 DIOL. Interfering plasma or CSF constituents are washed to waste using water containing 5% acetonitrile at a flow rate of 1.5 ml/min. After 5 min the flow is switched onto an analytical column and the drugs of interest are separated using methanol: acetonitrile: 0.008M phosphate buffer, pH 6.4 (188:578:235; V/V) for elution. NMR and mass spectral analysis confirms the isolation of (E)-N-didesmethyldoxepin and (Z)—N-didesmethyldoxepin.

Example 15

Isolation of (E)-2-O-glucuronyldoxepin and (E)-3-O-glucuronyldoxepin (E)-2-O-glucuronyldoxepin and (E)-3-O-glucuronyldoxepin are isolated from rat bile according to the methods described in the incorporated materials of Shu et al. (Drug Metabolism and Disposition (1990)18:1096-1099). Briefly, samples of rat bile are collected from rats for 4 hours after intraperitoneal injection with doxepin hydrochloride (28 mg/kg). The samples are chromatographed on a gradient HPLC system that consists of two solvent delivery pumps (Waters M045), a system controller (Waters Model 720), a UV absorbance detector (Waters Model 441), and an integrator (Hewlett 3390A). Chromotography is carried out on a column packed with Spherisorb nitrile (3 μm, 0.46×15 cm) and maintained at 50° C. The analysis begins with an initial isocratic period (1 min) with 95% solvent A (water) and 5% solvent B (acetonitrile/methanol, 75:25, v/v). Thereafter, a linear gradient elution is established by increasing the proportion of solvent B from 5% to 100% from 1 to 16 min, followed by a final period (4 min) of isocratic elution with 100% solvent B. The flow rate is 1.5 ml/min and UV absorbance is monitored at 254 nm with a sensitivity of 0.005 AUFS. NMR and mass spectral analysis confirms the isolation of (E)-2-O-glucuronyldoxepin and (E)-3-O-glucuronyldoxepin.

Example 16

Isolation of (Z)-2-O-glucuronyldoxepin and (Z)-3-O-glucuronyldoxepin (Z)-2-O-glucuronyldoxepin and (Z)-3-O-glucuronyldoxepin are isolated from rat bile according to the methods described above in Example 16 with the exception that the rats are injected with doxepin enriched for the cis (Z)-isomer of doxepin at a Z/E ratio of greater than 85:15. NMR and mass spectral analysis confirms the isolation of (Z)-2-O-glucuronyldoxepin and (Z)-3-O-glucuronyldoxepin.

Example 17

Preparation of (E)- and (Z)-doxepin N$^+$-glucuronide

The quaternary ammonium-linked glucuronide of doxepin (doxepin N$^+$-glucuronide) is obtained by organic synthesis as described in the incorporated materials of Luo et al. (Drug Metabolism and Disposition, (1991) 19:722-724). Briefly, the synthetic procedure involves quaternization of commercial samples of doxepin with methyl(2,3,4-tri-O-acetyl-1-bromo-1-deoxy-α-D-glucopyranosid)urinate, and subsequent removal of the protecting groups by treatment with sodium hydroxide. Thus, to prepare the (Z)-isomer of doxepin N$^+$-glucuronide, (Z)-doxepin is used as the starting material. To prepare the (E)-isomer of doxepin, (E)-doxepin is used as the starting material.

Example 18

Phase II Study to Evaluate Sleep Maintenance Effects of Three Dose Levels of Doxepin Hydrochloride (HCl) Relative to Placebo in Elderly Patients with Primary Insomnia A Phase II, randomized, multi-center, double-blind, placebo-controlled, four-period crossover, dose-response study was designed to assess the effects of doxepin (1 mg, 3 mg and 6 mg) compared with placebo in patients aged 65 years or older with primary sleep maintenance insomnia. Patients received a single-blind placebo for two consecutive nights during the PSG screening period, and double-blind study drug for two consecutive nights during each of the four treatment periods. Following each study drug administration, patients had 8 continuous hours of PSG recording in the sleep center. Patents were allowed to leave the sleep center during the day after each PSG assessment was complete. A 5- or 12-day study drug-free interval separated each PSG assessment visit. The duration of study participation per patient was approximately 7 to 11 weeks.

Patients who qualified for study entry, based on the screening PSG assessments, were randomized to a treatment sequence using a Latin square design. A final study visit was performed for patients either after completion of the four treatment periods or upon discontinuation from the study. Efficacy assessments were made at each visit and safety assessments were performed throughout the study.

Seventy-one patients were included in the per-protocol analysis set. The main inclusion criteria were male and/or female patients, aged 65 years or older, in good general health with at least a 3-month history of Diagnostic and Statistical Manual of Mental Disorders, fourth Edition (DSM-IV)-defined primary insomnia, reporting each of the following on four of seven nights prior to PSG screening: ≤6.5 hours of total sleep time (TST), ≥60 min of wakefulness after sleep onset (WASO) and ≥20 min of latency to sleep onset (LSO). Additionally, patients must have met the following entry criteria based on PSG assessments during the screening PSG period: wake time during sleep (WTDS) 60 min with no PSG screening night <45 min; TST>240 min and ≤410 min on both PSG screening nights; latency to persistent sleep (LPS)≥10 min on both PSG screening nights, <15 periodic limb movements with arousal per hour of sleep on the first PSG screening night, and <15 apnea/hypopneas per hour of sleep on the first PSG screening night. Doxepin HCl 1 mg, 3 mg and 6 mg capsules, and placebo capsules, were provided as a single dose for oral administration.

The primary efficacy assessment was WTDS. Secondary efficacy assessments included WASO, TST, SE and WTAS. All objective efficacy assessments were performed on Night 1 and Night 2

Efficacy analyses used the per-protocol (PP; the primary analysis set) sets. The PP analysis set included all patients who did not have important protocol derivations that would likely have effected the evaluation of efficacy, and who provided WTDS data from each of the four treatment periods. The primary and secondary efficacy analyses were based on the PP analysis set.

Within each treatment period, the average of the two data points was used for analysis, if applicable. The primary efficacy variable, WTDS, as well as the secondary objective parameters, was analyzed using an analysis of variance (ANOVA) model with terms for sequence, patient within sequence, treatment and period. Pairwise comparisons of each active treatment versus placebo were performed using Dunnett's test. All randomized patients who received at least one dose of double-blind study medication were included in the safety analyses, which were based on observed data.

Efficacy Results
Primary

WTDS exhibited a statistically significant decrease at the doxepin 1 mg (p=0.0001), 3 mg (p<0.0001) and 6 mg (p<0.0001) dose levels compared with placebo in the PP analysis set. The observed mean values (±SD) were: placebo 86.0 (38.15); doxepin 1 mg 70.1 (32.78); doxepin 3 mg 66.4 (31.56) and doxepin 6 mg 60.2 (28.00). The results using the ITT analysis set were consistent with those from the PP analysis set.

Secondary

The secondary PSG efficacy assessments are summarized in Table 1. WASO exhibited a statistically significant decrease at the doxepin 1 mg (p<0.0001), 3 mg (p<0.0001), and 6 mg (p<0.0001) dose levels compared to placebo. SE exhibited statistically significant increases at all three dose levels of doxepin (1 mg, p<0.0001; 3 mg, p<0.0001; 6 mg, p<0.0001) compared to placebo. TST exhibited statistically significant increases at all three dose levels of doxepin (1 mg, p<0.0001; 3 mg, p<0.0001; 6 mg, p<0.0001) compared to placebo. WTAS exhibited a statistically significant decrease at the doxepin 3 mg (p=0.0264) and 6 mg (p=0.0008) dose levels and numerically reduced at the doxepin 1 mg dose level, all compared to placebo.

TABLE 1

Secondary PSG Efficacy Assessments: Per-Protocol Analysis Set

| Parameter Per-Protocol (N = 71) | Placebo Mean | Doxepin 1 mg Mean | P-value[1] | Doxepin 3 mg Mean | P-value[1] | Doxepin 6 mg Mean | P-value[1] |
|---|---|---|---|---|---|---|---|
| SE (percent) | 74.9 | 78.5 | <0.0001 | 81.0 | <0.0001 | 82.8 | <0.0001 |
| TST (minutes) | 359.4 | 376.8 | <0.0001 | 388.8 | <0.0001 | 397.4 | <0.0001 |

TABLE 1-continued

Secondary PSG Efficacy Assessments: Per-Protocol Analysis Set

| Parameter Per-Protocol (N = 71) | Placebo Mean | Doxepin 1 mg Mean | P-value[1] | Doxepin 3 mg Mean | P-value[1] | Doxepin 6 mg Mean | P-value[1] |
|---|---|---|---|---|---|---|---|
| WTAS (minutes) | 13.0 | 10.4 | 0.5546 | 5.9 | 0.0264 | 5.0 | 0.0008 |
| WASO (minutes) | 99.0 | 80.5 | p<0.0001 | 72.3 | p<0.0001 | 65.2 | p<0.0001 |

[1]P-value comparing each active treatment versus placebo using Dunnett's test

SE was also analyzed for each hour of the night. The results are summarized in FIG. 2. Also, Table 2 summarizes the data for hours 7 and 8. With the exception of the hour 1 value for 1 mg, all three doxepin doses had numerically increased SE at each hour throughout the night compared to placebo, with statistically significant increased SE at several time points in the 3 and 6 mg dose levels. At the doxepin 6 mg dose level, SE exhibited statistically significant increases at hours 2, 4, 5, 6, 7 and 8. At the doxepin 3 mg dose level, SE exhibited statistically significant increases at hours 5, 6, 7 and 8. At the doxepin 1 mg dose level, SE exhibited statistically significant increases at hours 5 and 6.

TABLE 2

Sleep Efficiency for hours 7 and 8: per-protocol analysis set

| Parameter | Placebo | Doxepin 1 mg | Doxepin 3 mg | Doxepin 6 mg |
|---|---|---|---|---|
| Per-Protocol (N = 71) | | | | |
| Hour 7 SE (percent)[1] | | | | |
| Mean | 71.7 | 75.8 | 81.6 | 83.9 |
| P-value[2] | | 0.2376 | 0.0004 | <0.0001 |
| Hour 8 SE (percent)[1] | | | | |
| Mean | 63.2 | 64.8 | 73.1 | 74.8 |
| P-value[2] | | 0.9206 | 0.0009 | <0.0001 |

[1]Measurements taken from Night 1 and Night 2 were averaged. If one of the nights had a missing value, the n non-missing value was used.
[2]P-value comparing each active treatment versus placebo.

Conclusion

Doxepin 1 mg, 3 mg and 6 mg demonstrated efficacy on sleep maintenance parameters in elderly patients (65 years of age and older) with primary sleep maintenance insomnia, which appeared to be dose-related. Efficacy in delaying premature final awakenings was also demonstrated for doxepin 1 mg, 3 mg and 6 mg as evidenced by statistically significant reductions in WTAS at the doxepin 3 mg and 6 mg dose levels and numerical reductions at the doxepin 1 mg dose level, all compared to placebo. Also, efficacy in improving fragmented sleep at hours 7 and 8 was demonstrated for doxepin 1 mg, 3 mg, and 6 mg as evidenced by statistically significant increases in SE at hours 7 and 8 in the doxepin 3 mg and 6 mg dose levels and numerical reductions at 1 mg, all compared to placebo. All doxepin doses were well tolerated and demonstrated an adverse effect profile similar to placebo. There were no significant effects observed on next-day residual sedation. Sleep architecture was generally preserved.

Example 19

Phase II Study to Evaluate Sleep Maintenance Effects of Three Dose Levels of Doxepin Hydrochloride (HCl) Relative to Placebo in Adult Patients with Primary Insomnia A Phase II, randomized, multi-center, double-blind, placebo-controlled, four-period crossover, dose-response study was designed to assess the effects of doxepin (1 mg, 3 mg and 6 mg) compared with placebo in patients with primary sleep maintenance insomnia.

Patients received a single-blind placebo for two consecutive nights during the PSG screening period, and double-blind study drug for two consecutive nights during each of the four treatment periods. Following each study drug administration, patients had 8 continuous hours of PSG recording in the sleep center. Patents were allowed to leave the sleep center during the day after each PSG assessment was complete. A 5- or 12-day study drug-free interval separated each PSG assessment visit.

Patients who qualified for study entry, based on the screening PSG assessments, were randomized to a treatment sequence using a Latin square design. A final study visit was performed for patients either after completion of the four treatment periods or upon discontinuation from the study. Efficacy assessments were made at each visit and safety assessments were performed throughout the study.

Sixty-one patients were included in the per-protocol analysis set. The main inclusion criteria were male and/or female patients, aged 18 to 64 years, in good general health with at least a 3-month history of DSM-IV-defined primary insomnia, reporting each of the following on four of seven nights prior to PSG screening: ≤6.5 hours of total sleep time (TST), ≥60 min of WASO and ≥20 min of LSO. Additionally, patients must have met the following entry criteria based on PSG assessments during the screening PSG period: WTDS 60 min with no PSG screening night <45 min; TST>240 min and ≤410 min on both PSG screening nights; LPS 10 min on both PSG screening nights, <10 periodic limb movements with arousal per hour of sleep on the first PSG screening night, and <10 apnea/hypopneas per hour of sleep on the first PSG screening night. Doxepin HCl 1 mg, 3 mg and 6 mg capsules, and placebo capsules, were provided as a single dose for oral administration.

The primary and secondary efficacy assessments were as described above in Example 1. All objective efficacy assessments were performed on Night 1 and Night 2 of each treatment period. Statistical methods were as described in Example 1.

Efficacy Results
Primary

WTDS exhibited a statistically significant decrease at the doxepin 3 mg (p<0.0001) and 6 mg (p=0.0002) dose levels compared with placebo. WTDS was numerically, but not significantly decreased at the doxepin 1 mg dose level. The observed mean values (±SD) were: placebo 51.9 (42.25); doxepin 1 mg 43.2 (28.21); doxepin 3 mg 33.4 (21.87) and doxepin 6 mg 35.3 (25.17).

Secondary

The secondary PSG efficacy assessments are summarized in Table 3. SE exhibited statistically significant increases at all three dose levels of doxepin (1 mg, p=0.0004; 3 mg, p<0.0001; 6 mg, p<0.0001) compared to placebo. TST exhibited statistically significant increases at all three dose levels of doxepin (1 mg, p=0.0004; 3 mg, p<0.0001; 6 mg, p<0.0001) compared to placebo. WTAS exhibited a statistically significant decrease at the doxepin 6 mg dose level (p=0.0105) compared to placebo. There was a numerical decrease for WTAS at the doxepin 1 mg and 3 mg dose levels compared to placebo; these differences were not significant. WASO exhibited a statistically significant decrease at the doxepin 1 mg (0.0130), 3 mg (p<0.0001), and 6 mg (p<0.0001) dose levels compared to placebo.

TABLE 3

Secondary PSG Efficacy Assessments: Per-Protocol Analysis Set

| Parameter Per-Protocol (N = 61) | Placebo Mean | Doxepin 1 mg Mean | P-value[1] | Doxepin 3 mg Mean | P-value[1] | Doxepin 6 mg Mean | P-value[1] |
|---|---|---|---|---|---|---|---|
| SE (percent) | 80.7 | 84.7 | 0.0004 | 86.5 | <0.0001 | 86.9 | <0.0001 |
| TST (minutes) | 387.5 | 406.5 | 0.0004 | 415.2 | <0.0001 | 417.2 | <0.0001 |
| WTAS (minutes) | 10.2 | 4.1 | 0.1421 | 5.2 | 0.0697 | 2.5 | 0.0105 |
| WASO (minutes) | 62.1 | 47.3 | 0.0130 | 38.6 | <0.0001 | 38.8 | <0.0001 |

[1]P-value comparing each active treatment versus placebo using Dunnett's test

Figure 3:
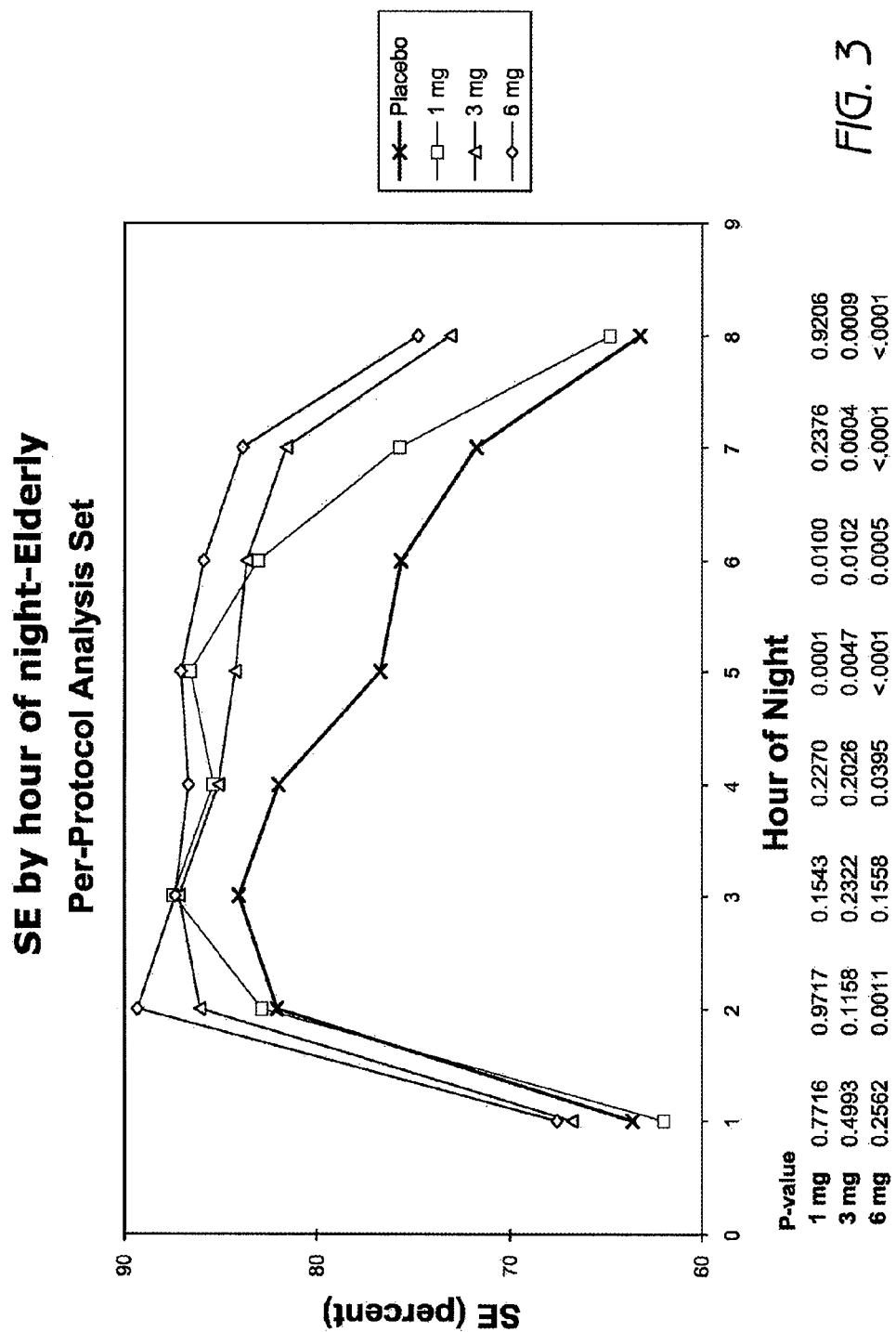
FIG. 3 is a graph showing sleep efficiency (SE) by hour of night in elderly adults after treatment with 1 mg, 3 mg and 6 mg doxepin (per-protocol data).

SE was also analyzed for each hour of the night. The results are summarized in FIG. 3. All three doxepin doses had numerically increased SE at each hour throughout the night compared to placebo, with statistically significant increased SE at several time points in the 3 and 6 mg dose levels. All three doxepin doses had significantly increased SE during the seventh and eighth hour of the night. The data for hours 7 and 8 are summarized in Table 4.

TABLE 4

Sleep Efficiency for Hours 7 and 8: per-protocol analysis set

| Parameter | Placebo | Doxepin 1 mg | Doxepin 3 mg | Doxepin 6 mg |
|---|---|---|---|---|
| Per-Protocol (N = 71) Hour 7 SE (percent)[1] | | | | |
| Mean | 79.9 | 88.2 | 89.6 | 90.4 |
| P-value[2] | | 0.0007 | 0.0001 | <0.0001 |
| Hour 8 SE (percent)[1] | | | | |
| Mean | 74.5 | 84.0 | 85.1 | 85.4 |
| P-value[2] | | 0.0018 | 0.0005 | 0.0003 |

[1]Measurements taken from Night 1 and Night 2 were averaged. If one of the nights had a missing value, the n on-missing value was used.
[2]P-value comparing each active treatment versus placebo.

Conclusion

Doxepin 1 mg, 3 mg and 6 mg demonstrated efficacy on sleep maintenance parameters in adult patients with primary sleep maintenance insomnia. Doxepin 1 mg, 3 mg and 6 mg demonstrated efficacy in preventing or delaying premature final awakenings as evidenced by significant reductions in WTAS at the doxepin 6 mg dose level and numerical reductions at the doxepin 1 mg and 3 mg dose levels, all compared to placebo. Also, efficacy in improving fragmented sleep at hours 7 and 8 was demonstrated for doxepin 1 mg, 3 mg, and 6 mg as evidenced by significant improvement to SE at hours 7 and 8 in all three doses, all compared to placebo. All doxepin doses were well tolerated and demonstrated an adverse effect profile similar to placebo. There were no significant effects on clinically meaningful alterations observed on next-day residual sedation and sleep architecture.

Example 20

Phase III Study to Evaluate Sleep Maintenance Effects of Doxepin Hydrochloride (HCl) Relative to Placebo in Patients with Primary Insomnia A Phase III, randomized, double-blind, placebo-controlled, parallel-group, multicenter study was performed to assess the efficacy and safety of Doxepin HCl at two dosages, 3 mg and 6 mg, in primary insomnia patients with sleep maintenance difficulties. Patients with a 3-month history of primary insomnia, according to Diagnostic and Statistical Manual of Mental Disorders, Fourth Edition Text Revision (DSM-IV-TR)-defined primary insomnia were enrolled.

This was a randomized, double-blind, placebo-controlled, parallel-group study designed to assess the efficacy and safety of two dose levels of doxepin, 3 mg and 6 mg, in subjects with primary insomnia and sleep maintenance difficulties. Efficacy and safety assessments were conducted throughout the study. Doxepin 3 mg and 6 mg capsules, and placebo capsules, were provided as a single dose for oral administration. Sleep efficiency (SE) was evaluated. Data were analyzed as randomized and based on observed cases.

Diagnosis and Main Criteria for Inclusion

Subjects were females and males, 18 to 64 years of age inclusive, with at least a 3-month history of primary insomnia (as defined in the Diagnostic and Statistical Manual of Mental Disorders, Fourth Edition, Text Revision), who reported experiencing ≥60 minutes of Wake After Sleep Onset (WASO), ≥20 minutes of Latency to Sleep Onset (LSO), and ≤6.5 hours of Total Sleep Time (TST) on at least 4 of 7 consecutive nights prior to PSG Screening.

Criteria for Evaluation:

Primary Efficacy Variable: The primary efficacy variable was WASO on Night 1.

Additional Objective Variables: Additional efficacy variables obtained during each PSG recording night during the Double-blind Treatment Period were Wake Time During Sleep (WTDS), TST, Sleep Efficiency (SE) overall, SE by third of the night, SE by hour of the night, Latency to Persistent Sleep (LPS), latency to Stage 2 sleep, Number of Awakenings After Sleep Onset (NAASO), Total Wake Time (TWT), Wake Time After Sleep (WTAS), and sleep architecture (including percentage and minutes of Stage 1, 2, and 3-4 sleep; percentage of rapid eye movement [REM] and non-REM sleep; and latency to REM sleep).

Subjective Variables: Subjective efficacy variables were subjective TST (sTST), subjective WASO (sWASO), LSO, subjective NAASO (sNAASO), and sleep quality. These variables were assessed using a questionnaire completed in the morning following each PSG recording night. Drowsiness, ability to function, and total nap time during the day were assessed using an evening questionnaire completed on Night 2, Night 16, and Night 30. Other secondary subjective efficacy variables included the 2-item Clinical Global Impressions (CGI) scale for severity and therapeutic effect completed by a clinician; the 5-item CGI scale pertaining to therapeutic effect completed by the subject; the Insomnia Severity Index (ISI) completed by the subject; and a subjective assessment of average nightly total sleep time following administration of the study drug at home.

A total of 229 subjects were randomized into the study (76 to placebo, 77 to 3 mg, and 76 to 6 mg). These groups were comparable with respect to weight, height, gender and baseline sleep characteristics. A total of 203 (89%) subjects completed the study, with comparable early termination rates across treatment groups.

Summary of Results:

Of the 229 randomized subjects, 203 (89%) completed the study and 26 (11%) withdrew from the study. Early termination rates and baseline characteristics were comparable across treatment groups. The study population was female (73%) and male (27%). The mean age was 44.5 years. Subjects were White (48%), Black/African American (33%), Hispanic (16%), Asian (1%), and Other (2%).

Efficacy Results:

Primary Efficacy Variable (WASO on Night 1) Using the a priori ITT Analysis Set

Mean WASO on Night 1 was statistically significantly decreased by approximately 25 to 30 minutes following administration of doxepin 3 mg and 6 mg compared with placebo. Additionally, the mean WASO was statistically significantly decreased by approximately 15 to 20 minutes in each doxepin group compared with placebo through 29 nights of treatment. Similar results for WASO were observed for the average of Nights 1, 15, and 29 as well as for the means of the paired study nights (Nights 1 and 2; Nights 15 and 16; and Nights 29 and 30).

Figure 4:
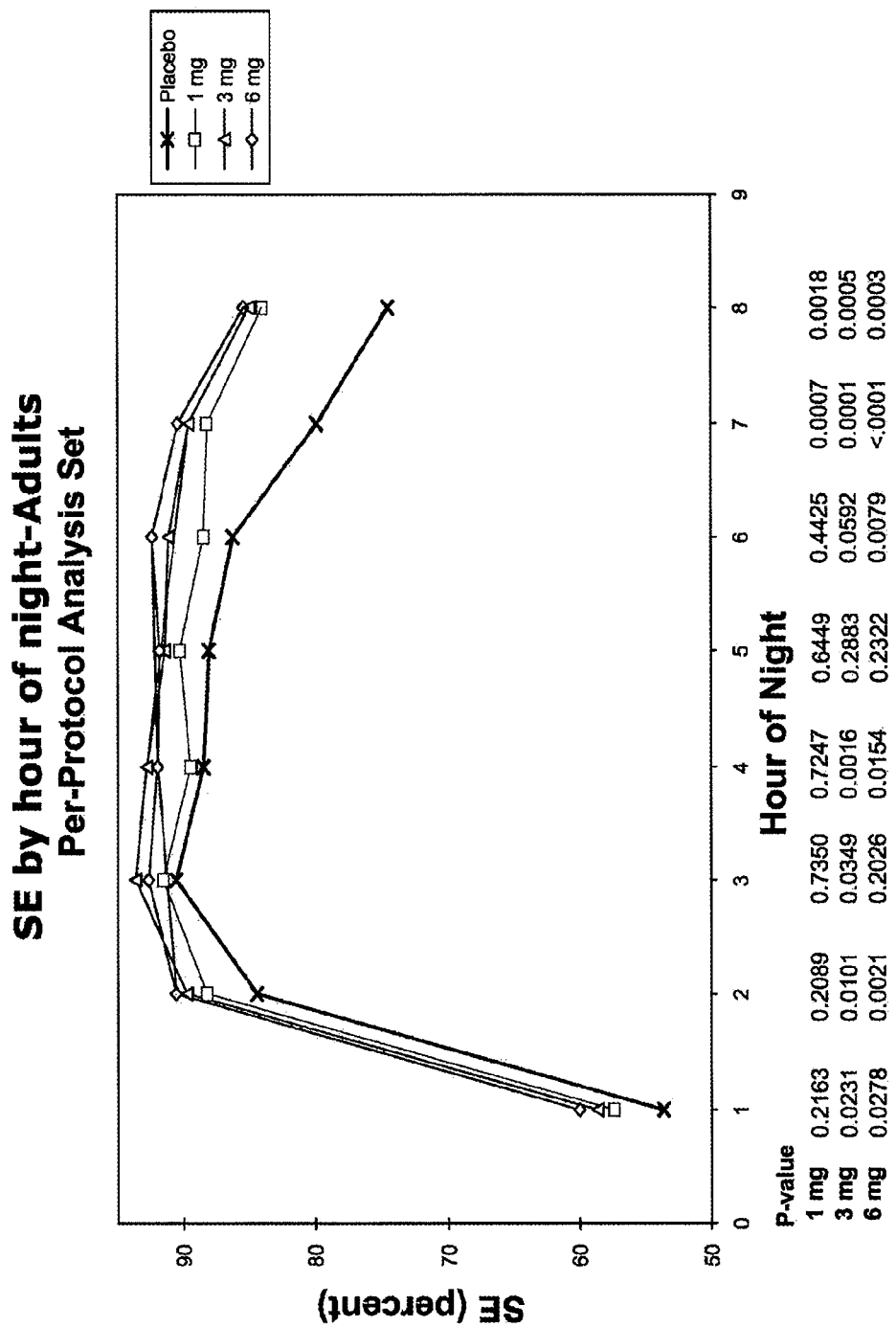
FIG. 4 is a graph showing SE by hour of night in adults (18-64 years old) treated with 1 mg, 3 mg or 6 mg doxepin.
Figure 5:
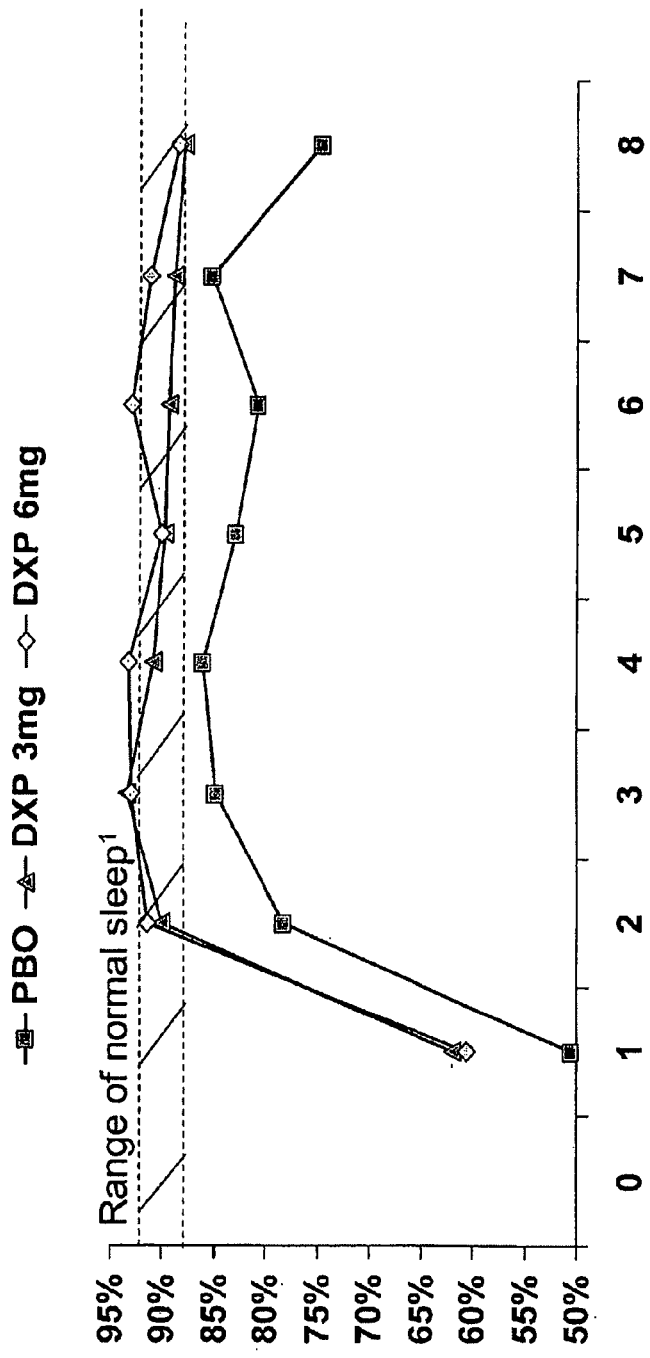
FIG. 5 is a graph showing SE by hour of night in adults treated with placebo, 3 mg doxepin or 6 mg doxepin.

There were consistent, statistically significant improvements for doxepin 3 mg and 6 mg compared to placebo in SE second third-of-night and SE final-third-of-night. In particular, SE at hours 7 and 8 of the 8 hour period of sleep surprisingly exhibited statistically significant increases by treatment with low-dose doxepin. These results are shown in Tables 5-7, respectively. The results also are graphically depicted in FIGS. 4 and 5.

TABLE 5

Key Objective Efficacy Variables on Night 1 and Night 29

| PSG Variable | Placebo (N = 72) | Doxepin 3 mg (N = 75) | Doxepin 6 mg (N = 73) |
| --- | --- | --- | --- |
| TST (minutes) | | | |
| Baseline | 380.3 (44.70) | 380.3 (46.09) | 380.3 (43.09) |
| Night 1 | 373.8 (72.22) | 415.3 (41.65) | 420.5 (37.07) |
| | | $p < 0.0001$ | $p < 0.0001$ |
| Night 29 | 391.0 (50.50) | 408.1 (52.41) | 419.1 (44.98) |
| | | $p = 0.0262$ | $p = 0.0003$ |
| SE Overall (%) | | | |
| Baseline | 79.2 (9.31) | 79.2 (9.60) | 79.2 (8.98) |
| Night 1 | 77.9 (15.05) | 86.5 (8.68) | 87.6 (7.72) |
| | | $p < 0.0001$ | $p < 0.0001$ |
| Night 29 | 81.5 (10.52) | 85.0 (10.92) | 87.3 (9.37) |
| | | $p = 0.0262$ | $p = 0.0003$ |
| SE in Hour 8 (%) | | | |
| Baseline | 78.0 (18.92) | 74.9 (22.87) | 76.4 (21.26) |
| Night 1 | 74.5 (29.15) | 87.8 (14.28) | 88.4 (14.25) |
| | | $p < 0.0001$ | $p < 0.0001$ |
| Night 29 | 75.4 (26.06) | 81.9 (20.81) | 85.8 (19.66) |
| | | $p = 0.0524$ | $p = 0.0034$ |
| WTAS (minutes) | | | |
| Baseline | 5.8 (12.72) | 8.5 (16.95) | 5.2 (9.22) |
| Night 1 | 6.4 (15.52) | 0.7 (3.71) | 1.1 (4.60) |
| | | $p = 0.0002$ | $p = 0.0030$ |
| Night 29 | 5.8 (15.57) | 3.2 (8.42) | 2.7 (9.92) |
| | | $p = 0.2104$ | $p = 0.2448$ |
| LPS (minutes)[1] | | | |
| Baseline | 38.0 (28.56) | 35.9 (29.84) | 39.1 (34.10) |
| Night 1 | 45.0 (54.91) | 26.7 (23.42) | 27.1 (25.42) |
| | | $p = 0.0110$ | $p = 0.0018$ |
| Night 29 | 31.3 (35.98) | 28.0 (25.99) | 24.7 (21.48) |
| | | $p = 0.9008$ | $p = 0.9989$ |

Data presented are mean (SD).

p-value comparing each active treatment versus placebo was determined from an ANCOVA model that included main effects for treatment and center with the baseline value as a covariate using Dunnett's test.

[1]Analysis performed on log-transformed data.

Sleep Efficiency

Sleep Efficiency Overall

There were statistically significant increases in mean SE overall on Night 1 for the doxepin groups compared with placebo and Night 29 (3 mg and 6 mg groups). Additionally, there were statistically significant increases in mean SE overall for the average of Nights 1, 15, and 29 for each doxepin group compared with placebo.

TABLE 6

SE Overall at Baseline, Night 1, Night 29, and the
Average of Nights 1, 15, and 29: ITT Analysis Set

| Sleep Efficiency Overall (%) | Placebo (N = 72) | Doxepin 3 mg (N = 75) | Doxepin 6 mg (N = 73) |
|---|---|---|---|
| Baseline (Mean of Nights -6 and -5) | n = 72 | n = 75 | n = 73 |
| Mean (SD) | 79.2 (9.31) | 79.2 (9.60) | 79.2 (8.98) |
| Median (Range) | 80.5 (52.3-95.7) | 81.4 (53.0-94.7) | 79.4 (56.9-94.1) |
| Night 1 (Visit 4) | n = 72 | n = 75 | n = 73 |
| Mean (SD) | 77.9 (15.05) | 86.5 (8.68) | 87.6 (7.72) |
| Median (Range) | 81.1 (14.3-97.6) | 89.2 (54.4-97.6) | 90.5 (62.9-98.4) |
| Diff. of LS Mean (Std. Err) | | 8.6 (1.46) | 9.8 (1.46) |
| 95% CI of LS mean Diff. | | (5.3, 11.8) | (6.6, 13.1) |
| p-value[1] | | p < 0.0001 | p < 0.0001 |
| Night 29 (Visit 6) | n = 68 | n = 68 | n = 69 |
| Mean (SD) | 81.5 (10.52) | 85.0 (10.92) | 87.3 (9.37) |
| Median (Range) | 82.6 (54.6-96.1) | 88.0 (27.5-97.0) | 89.8 (52.4-98.4) |
| Diff. of LS Mean (Std. Err) | | 3.8 (1.52) | 5.8 (1.51) |
| 95% CI of LS mean Diff. | | (0.4, 7.1) | (2.5, 9.2) |
| p-value[1] | | p = 0.0262 | p = 0.0003 |
| Average of Nights 1, 15, and 29 | n = 72 | n = 75 | n = 73 |
| Mean (SD) | 80.2 (11.03) | 85.1 (8.95) | 86.9 (7.66) |
| Median (Range) | 81.1 (45.0-95.8) | 86.6 (50.2-97.6) | 88.7 (69.1-96.7) |
| p-value[1] | | p = 0.0001 | p < 0.0001 |

[1]p-value comparing each active treatment versus placebo was determined from an ANCOVA model that included main effects for treatment and center with the baseline value as a covariate using Dunnett's test.

Sleep Efficiency: Final Third of the Night

Statistically significant improvements in the mean SE value from the final third of the night on Night 1 were observed for each doxepin group, 3 mg and 6 mg, compared with placebo and were sustained on Night 15 (3 mg and 6 mg groups) and Night 29 (6 mg group).

TABLE 7

SE Final Third of the Night at Baseline,
Night 1 and Night 29: ITT Analysis Set

| Sleep Efficiency (%) | Placebo (N = 72) | Doxepin 3 mg (N = 75) | Doxepin 6 mg (N = 73) |
|---|---|---|---|
| SE Final Third of the Night (%) | | | |
| Baseline (Mean of Nights -6 and -5) | n = 72 | n = 75 | n = 73 |
| Mean (SD) | 79.4 (13.05) | 80.3 (13.43) | 80.7 (13.12) |
| Night 1 (Visit 4) | n = 72 | n = 75 | n = 73 |
| Mean (SD) | 79.8 (17.85) | 88.4 (13.89) | 90.6 (7.73) |
| p-value[1] | | P = 0.0002 | p < 0.0001 |
| Night 29 (Visit 6) | n = 68 | n = 68 | n = 69 |
| Mean (SD) | 81.6 (14.11) | 86.0 (12.90) | 89.1 (11.93) |
| p-value[1] | | P = 0.0838 | p = 0.0007 |

[1]p-value comparing each active treatment to placebo was determined from an ANCOVA model that included main effects for treatment and center with the baseline value as a covariate using Dunnett's test.

Sleep Efficiency by Hour of the Night

Figure 7:
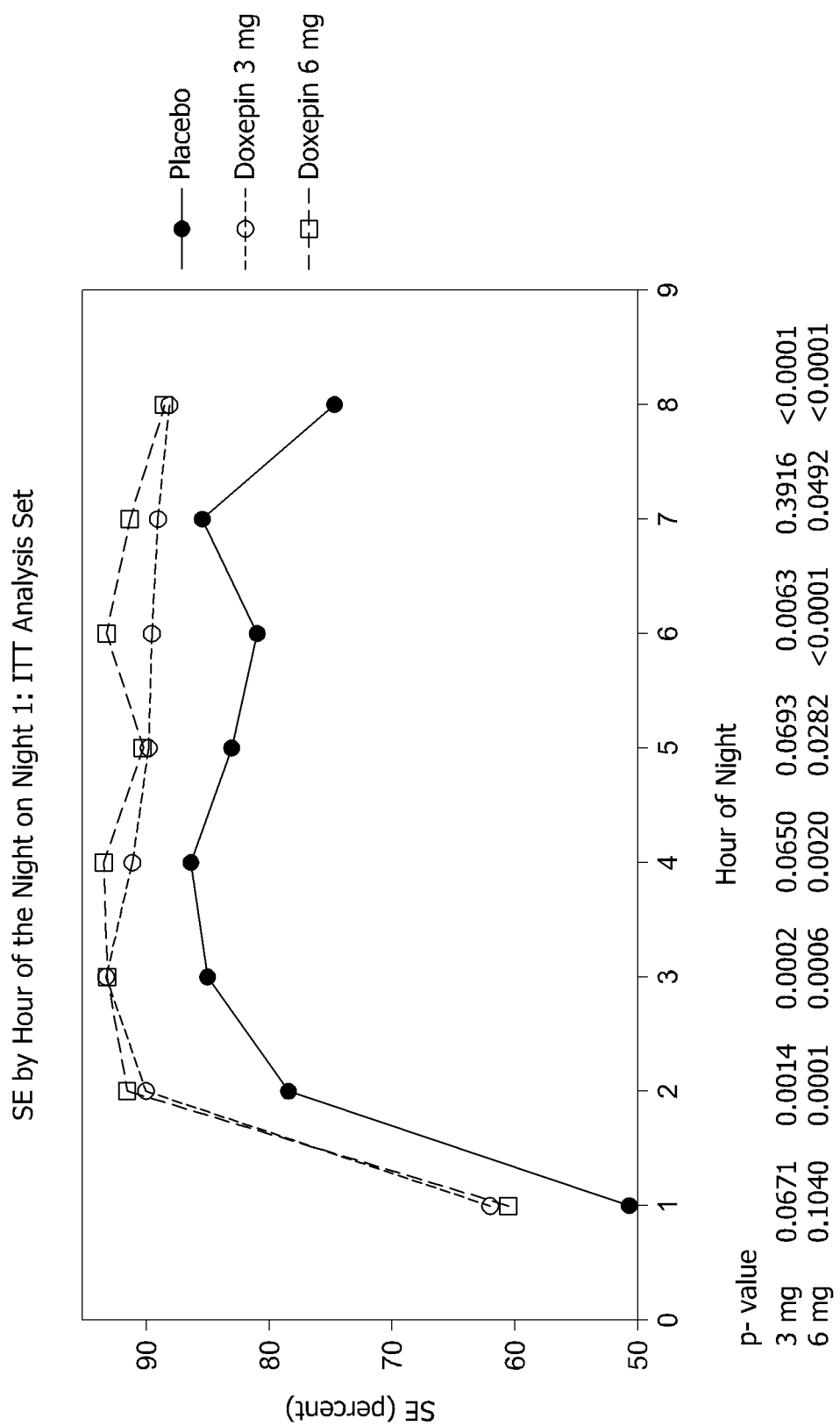
FIG. 7 is a graph showing SE by Hour of the Night on Night 1: ITT Analysis Set.
Figure 8:
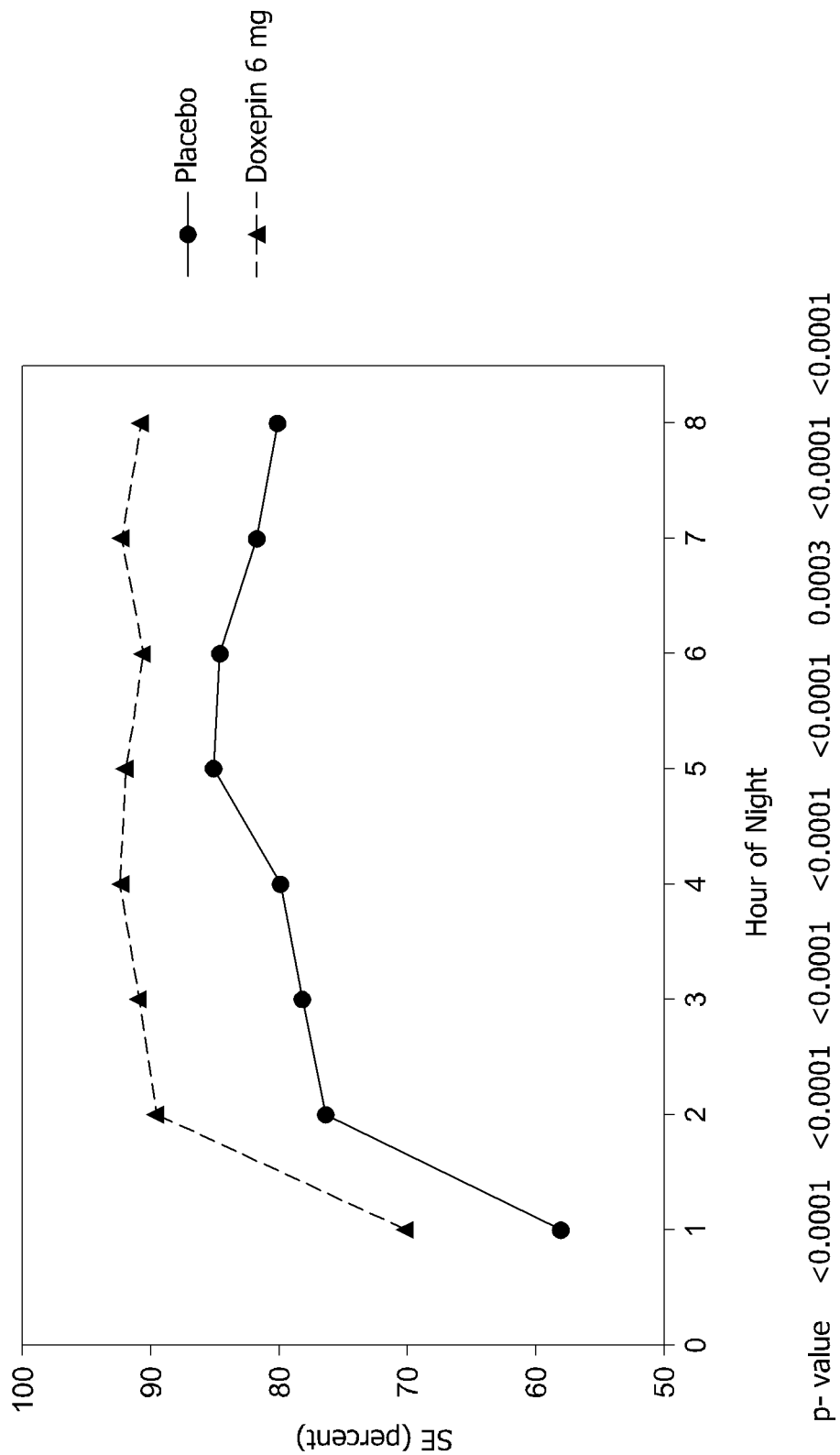
FIG. 8 is a graph showing SE by hour of night in adults with transient insomnia treated with 6 mg doxepin.

Sleep efficiency by hour of the night on Night 1, adjusted for multiple comparisons using Dunnett's test, is displayed in FIG. 7.

Sleep efficiency by hour of the night for each doxepin group, 3 mg and 6 mg, compared with placebo was improved significantly at most assessment timepoints on Night 1 including Hour 8 (p<0.0001).

Sleep Efficiency in Hour 8

The mean SE in Hour 8 was 87.8% and 88.4% for the doxepin 3 mg and 6 mg groups, respectively, versus 74.5% for the placebo group, as presented in Table 8.

TABLE 8

SE in Hour 8 at Baseline, Night 1 and Night 29: ITT Analysis Set

| Sleep Efficiency in Hour 8 (%) | Placebo (N = 72) | Doxepin 3 mg (N = 75) | Doxepin 6 mg (N = 73) |
|---|---|---|---|
| Baseline (Mean of Nights -6 and -5) | n = 72 | n = 75 | n = 73 |
| Mean (SD) | 78.0 (18.92) | 74.9 (22.87) | 76.4 (21.26) |
| Median (Range) | 84 (22.5-98.3) | 82.5 (1.7-99.6) | 84.2 (18.8-99.2) |
| Night 1 (Visit 4) | n = 72 | n = 75 | n = 73 |
| Mean (SD) | 74.5 (29.15) | 87.8 (14.28) | 88.4 (14.25) |
| Median (Range) | 89.2 (0.0-100.0) | 94.2 (26.7-100.0) | 93.3 (30.0-100.0) |
| Diff. of LS Mean (Std. Err) | | 14.1 (3.21) | 14.3 (3.23) |
| 95% CI of LS mean Diff. | | (6.9, 21.3) | (7.2, 21.5) |
| p-value[1] | | p < 0.0001 | p < 0.0001 |
| Night 29 (Visit 6) | n = 68 | n = 68 | n = 69 |
| Mean (SD) | 75.4 (26.06) | 81.9 (20.81) | 85.8 (19.66) |
| Median (Range) | 85.0 (0.0-100.0) | 90.4 (14.2-100.0) | 94.2 (0.0-100.0) |

TABLE 8-continued

SE in Hour 8 at Baseline, Night 1 and Night 29: ITT Analysis Set

| Sleep Efficiency in Hour 8 (%) | Placebo (N = 72) | Doxepin 3 mg (N = 75) | Doxepin 6 mg (N = 73) |
|---|---|---|---|
| Diff. of LS Mean (Std. Err) | | 8.0 (3.61) | 11.3 (3.57) |
| 95% CI of LS mean Diff. | | (−0.1, 16.0) | (3.4, 19.3) |
| p-value[1] | | p = 0.0524 | p = 0.0034 |

[1]p-value comparing each active treatment to placebo was determined from an ANCOVA model that included main effects for treatment and center with the baseline value as a covariate using Dunnett's test.

Example 21

Phase III Study to Evaluate Sleep Maintenance Effects of Doxepin Hydrochloride (HCl) Relative to Placebo in Patients with Transient Insomnia A Phase III, Randomized, Double-Blind, Placebo-Controlled, Parallel-Group, Multicenter Study was conducted to assess the efficacy and safety of doxepin HCl for the treatment of transient insomnia in adult subjects.

This randomized, double-blind, placebo-controlled, parallel-group, single-dose study was designed to evaluate the effects of doxepin 6 mg in adult subjects. A laboratory adaptation model (i.e., first night effect) combined with a 3-hour phase advance was implemented to induce transient insomnia in healthy adult subjects.

Diagnosis and Main Criteria for Inclusion:

Subjects were healthy females and males, 25 to 55 years of age inclusive, with an Epworth Sleepiness Scale score ≤12 at screening, and a 3-month history of normal nightly sleep. Eligibility also was determined using protocol-defined criteria based on sleep diary information obtained during the 7-day period before randomization.

Criteria for Evaluation:

Primary Efficacy Variable: The primary efficacy variable was Latency to Persistent Sleep (LPS) on Night 1.

Key Secondary Efficacy Variable: The key secondary efficacy variable was Wake After Sleep Onset (WASO) on Night 1.

Additional Objective Variables: Additional PSG variables obtained on Night 1 were Total Sleep Time (TST); Total Wake Time (TWT) overall and by hour of the night; Sleep Efficiency (SE) overall, by third of the night, by hour of the night, and last quarter of the night; latency to Stage 2 sleep; Wake Time During Sleep (WTDS); Wake Time After Sleep (WTAS); Number of Awakenings After Sleep Onset (NAASO) overall and by hour of the night; and sleep architecture including percentages and minutes of Stage 1, 2, and 3-4 sleep, percentages and minutes of rapid eye movement (REM) sleep and non-REM sleep, and latency to REM sleep.

Subjective Variables: Subjective variables, obtained from a questionnaire completed during the morning of Day 2, were Latency to Sleep Onset (LSO), subjective TST (sTST), subjective NAASO (sNAASO), subjective WASO (sWASO), and sleep quality.

Summary of Results:

All 565 randomized subjects (282 in the placebo group and 283 in the doxepin 6 mg group) completed the study. Demographic and other baseline characteristics were similar between the two treatment groups. Subjects were female (55%) and male (45%). The mean age was 35.5 years. Subjects were White (50%), Hispanic (32%), Black/African American (15%), Asian (1%), Native Hawaiian or other Pacific Islander (<1%), and Other (1%).

Efficacy Results:

Primary and Key Secondary Objective Efficacy Variables

Administration of doxepin 6 mg resulted in statistically significant improvements in LPS (primary efficacy variable) and WASO on Night 1 (key secondary efficacy variable) when compared with placebo. Improvements in LPS and WASO were independent of gender and race/ethnicity.

TABLE 9

Primary and Key Secondary Objective PSG Variables on Night 1: ITT Analysis Set

| PSG Variable | Placebo (N = 282) | Doxepin 6 mg (N = 283) | p-value[1] |
|---|---|---|---|
| LPS (minutes) - Primary | n = 282 | n = 283 | |
| LS Mean (Std. Err.) | 32.9 (1.83) | 20.0 (1.83) | p < 0.0001 |
| WASO (minutes) - Key Secondary | n = 281 | n = 281 | |
| LS Mean (Std. Err.) | 79.4 (3.11) | 40.4 (3.11) | p < 0.0001 |

[1]p-value for comparing treatments was determined from an ANOVA model that included main effects for treatment and center.

Additional Secondary Objective Efficacy Variables

There were statistically significant improvements in the objective efficacy variables including TST, TWT, SE, latency to Stage 2 sleep, WTDS, and WTAS following administration of doxepin 6 mg when compared with placebo. The analyses by hour of the night for SE and TWT were statistically significant for doxepin 6 mg compared with placebo at all timepoints. Improvements in TWT were distributed evenly across all hours of the night for the doxepin 6 mg group.

There were no clinically meaningful effects for doxepin 6 mg on sleep architecture; sleep stages were preserved compared with placebo. Minutes spent in Stage 2 and Stage 3-4 sleep were greater in the doxepin 6 mg group than in the placebo group with no difference between treatment groups in minutes spent in REM sleep.

TABLE 10

Additional Objective PSG Variables on Night 1: ITT Analysis Set

| PSG Variable | Placebo (n = 281) | Doxepin 6 mg (n = 281) | p-value[1] |
|---|---|---|---|
| WTDS (minutes) | | | |
| LS Mean (Std. Err.) | 74.0 (3.02) | 39.8 (3.02) | p < 0.0001 |
| WTAS (minutes) | | | |
| LS Mean (Std. Err.) | 5.4 (0.90) | 0.6 (0.90) | p < 0.0001 |
| TST (minutes) | | | |
| LS Mean (Std. Err.) | 372.6 (3.58) | 423.6 (3.58) | p < 0.0001 |

TABLE 10-continued

Additional Objective PSG Variables on Night 1: ITT Analysis Set

| PSG Variable | Placebo (n = 281) | Doxepin 6 mg (n = 281) | p-value[1] |
|---|---|---|---|
| SE - Overall (%) | | | |
| LS Mean (Std. Err.) | 77.6 (0.75) | 88.3 (0.75) | p < 0.0001 |
| LS Mean (Std. Err.) | 69.5 (1.17) | 82.5 (1.17) | p < 0.0001 |
| LS Mean (Std. Err.) | 81.8 (0.99) | 91.2 (0.99) | p < 0.0001 |
| SE - Final Third of the Night (%) | | | |
| LS Mean (Std. Err.) | 81.6 (1.07) | 91.1 (1.07) | p < 0.0001 |
| SE - Last Quarter of the Night (%) | | | |
| LS Mean (Std. Err.) | 81.2 (1.15) | 91.7 (1.15) | p < 0.0001 |
| TWT (minutes) | | | |
| LS Mean (Std. Err.) | 107.4 (3.58) | 56.4 (3.58) | p < 0.0001 |

[1]p-value comparing doxepin 6 mg treatment versus placebo was determined from an ANOVA model that included main effects for treatment and center.

Step-down Procedure for Primary and Key Secondary Efficacy Variables: Comparison of the doxepin 6 mg group to placebo with respect to LPS was statistically significant. Therefore, the comparison with respect to WASO was performed. Similarly, there was a statistically significant improvement in WASO following administration of doxepin 6 mg when compared with placebo.

Sensitivity Analyses for Primary and Key Secondary Efficacy Variables: For both sensitivity analyses for LPS and WASO, results for the doxepin 6 mg group compared with placebo were statistically significant (p<0.0001) and similar to results for observed cases using the ITT analysis set.

Subjective Efficacy Variables: There were statistically significant improvements in all subjective efficacy variables (LSO, sTST, sWASO, sNAASO, and sleep quality) on Day 2 following administration of doxepin 6 mg when compared with placebo.

Conclusions:

Administration of doxepin 6 mg when compared with placebo resulted in statistically significant and clinically meaningful effects on objective measures and all subjective measures used in this study to assess sleep onset, sleep maintenance, and prevention of early morning awakenings. Doxepin 6 mg was safe and well-tolerated following single-dose administration with an AE profile comparable to placebo.

Efficacy and safety results for doxepin 6 mg compared with placebo include:

Statistically significant effects (p<0.0001) on both objective and subjective measures of sleep onset, as assessed by LPS (primary efficacy variable) and LSO. The LS mean for LPS was 13.0 minutes shorter for the doxepin 6 mg group compared with the placebo group. The geometric LS mean for LSO was 23.4 minutes for the doxepin 6 mg group compared with 31.7 minutes for the placebo group.

Statistically significant effects on multiple objective and subjective measures of sleep maintenance, including WASO (key secondary efficacy variable), TST, SE overall, SE by hour of the night, WTDS, TWT overall, TWT by hour of the night, sTST, and sWASO. Results for the objective and subjective assessments were consistent, although in some instances (i.e., TST and WASO) the subjective ratings underestimated the magnitude of effects seen with the PSG measures of the same variables.

Statistically significant improvements m preventing early morning awakenings as assessed using PSG variables, including SE in Hours 7 and 8, WTAS, and SE in the last quarter of the night.

The number of awakenings and TWT were distributed evenly across the hours of the night for doxepin after Hour 1.

No clinically meaningful effects on sleep architecture; sleep stages were preserved No clinically meaningful next day hangover/residual effects.

There were no reports of potentially anticholinergic AEs or memory impairment-associated AEs in the doxepin 6 mg group.

There were no clinically meaningful mean changes noted in laboratory test values, vital sign measurements, ECGs, physical examinations, or neurological assessments. There was a low incidence of AEs associated with laboratory values in both treatment groups.

Sleep Efficiency
Sleep Efficiency—Overall

There was a statistically significant improvement in the mean SE (overall) for the doxepin 6 mg group compared with the placebo group. The LS mean SE was greater (improved) for the doxepin 6 mg group by 10.6% compared with the placebo group. The SE results are shown in Table 11.

TABLE 11

SE Overall and by First, Second, and Final Third of the Night on Night 1: ITT Analysis Set

| SE Variable | Placebo (N = 282) | Doxepin 6 mg (N = 283) |
|---|---|---|
| SE - Overall (%) | n = 281 | n = 281 |
| Mean (SD) | 77.9 (14.47) | 88.6 (8.32) |
| Median (Range) | 80.6 (18.2-98.3) | 91.0 (35.0-99.3) |
| LS Mean (Std. Err.) | 77.6 (0.75) | 88.3 (0.75) |
| Difference of LS Mean (Std. Err.) | | 10.6 (0.99) |
| 95% CI of LS Mean Difference | | (8.7, 12.6) |
| p-value[1] | | p < 0.0001 |
| 95% CI of LS Mean Difference | | (6.8, 12.0) |
| p-value[1] | | p < 0.0001 |
| SE-Final Third of the Night (%) | n = 281 | n = 281 |
| Mean (SD) | 81.7 (22.02) | 91.2 (9.48) |
| Median (Range) | 91.9 (1.6-100.0) | 94.1 (29.4-100.0) |
| LS Mean (Std. Err.) | 81.6 (1.07) | 91.1 (1.07) |
| Difference of LS Mean (Std. Err.) | | 9.5 (1.43) |
| 95% CI of LS Mean Difference | | (6.7, 12.3) |
| p-value[1] | | p < 0.0001 |

[1]p-value for comparing treatments was determined from an ANOVA model that included main effects for treatment and center.

Sleep Efficiency—Final Third of the Night

There was a statistically significant improvement in mean SE for the final third of the night for the doxepin 6 mg group compared with placebo. The LS mean SE was 9.5% greater (improved) for the doxepin 6 mg group compared with the placebo group.

Sleep Efficiency in the Last Quarter of the Night

A summary of SE in the last quarter of the night by treatment group using the ITT analysis set is presented in Table 12.

There was a statistically significant improvement in mean SE in the last quarter of the night for the doxepin 6 mg group compared with the placebo group. The LS mean SE in the last quarter of the night was 10.4% greater (improved) for the doxepin 6 mg group compared with the placebo group.

TABLE 12

SE in the Last Quarter of the Night on Night 1: ITT Analysis Set

| SE - Last Quarter of the Night (%) | Placebo (N = 282) | Doxepin 6 mg (N = 283) |
|---|---|---|
| Subjects | n = 281 | n = 281 |
| Mean (SD) | 81.0 (23.80) | 91.4 (9.69) |
| Median (Range) | 92.5 (0.0-100.0) | 94.6 (33.3-100.0) |
| LS Mean (Std. Err.) | 81.2 (1.15) | 91.7 (1.15) |
| Difference of LS Mean (Std. Err.) | | 10.4 (1.53) |
| 95% CI of LS Mean Difference | | (7.4, 13.4) |
| p-value[1] | | p < 0.0001 |

[1]p-value for comparing treatments was determined from an ANOVA model that included main effects for treatment and center.

Sleep Efficiency by Hour of the Night

Figure 6:
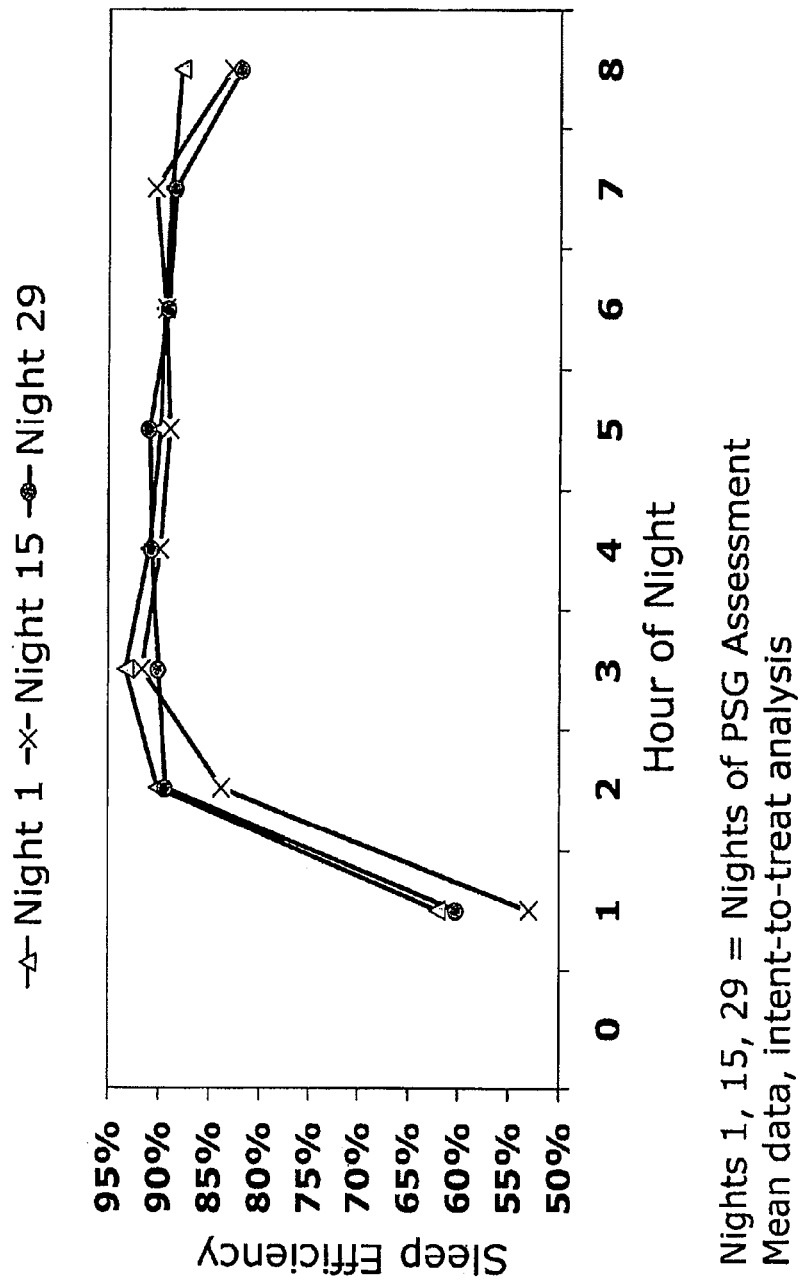
FIG. 6 is a graph showing SE by hour of night on nights 1, 15 and 29 in adults treated with 3 mg doxepin or 6 mg doxepin.

Sleep Efficiency by hour for the doxepin 6 mg group compared with placebo was statistically significantly improved at all timepoints (p<0.0003). Sleep Efficiency by hour of the night on Night 1 is presented in FIG. 6.

Sleep efficiency in Hour 7 using the ITT analysis set is presented in Table 13.

Sleep efficiency in Hour 8 using the ITT analysis set is presented in Table 14.

TABLE 13

SE in Hour 7 on Night 1: ITT Analysis Set

| SE-Hour 8 (%) | Placebo (N = 282) | Doxepin 6 mg (N = 283) |
|---|---|---|
| Subjects | n = 281 | n = 281 |
| Mean (SD) | 81.6 (27.47) | 92.0 (12.19) |
| Median (Range) | 93.3 (0.0-100.0) | 95.8 (0.0-100.0) |
| LS Mean (Std. Err.) | 81.6 (1.34) | 91.9 (1.34) |
| Difference of LS Mean (Std. Err.) | | 10.4 (1.79) |
| 95% CI of LS Mean Difference | | (6.9, 13.9) |
| p-value[1] | | p < 0.0001 |

[1]p-value for comparing treatments was determined from an ANOVA model that included main effects for treatment and center.

TABLE 14

SE in Hour 8 on Night 1: ITT Analysis Set

| SE-Hour 8 (%) | Placebo (N = 282) | Doxepin 6 mg (N = 283) |
|---|---|---|
| Subjects | n = 281 | n = 281 |
| Mean (SD) | 80.4 (27.86) | 90.9 (12.70) |
| Median (Range) | 94.2 (0.0-100.0) | 95.0 (10.8-100.0) |
| LS Mean (Std. Err.) | 81.0 (1.37) | 91.5 (1.37) |
| Difference of LS Mean (Std. Err.) | | 10.5 (1.83) |
| 95% CI of LS Mean Difference | | (6.9, 14.0) |
| p-value[1] | | p < 0.0001 |

[1]p-value for comparing treatments was determined from an ANOVA model that included main effects for treatment and center.

Many modifications and variations of the embodiments described herein may be made without departing from the scope, as is apparent to those skilled in the art. The specific embodiments described herein are offered by way of example only.

We claim:

1. A method for treating insomnia, the method comprising:
administering an oral formulation comprising doxepin or a pharmaceutically acceptable salt thereof to a patient in need thereof, wherein the patient is aged 18 years to 64 years, wherein the oral formulation comprises one or more tablets or one or more capsules for a total dosage of doxepin of 6 mg, and wherein the oral formulation is administered prior to bedtime.

2. The method of claim 1, wherein administering the oral formulation is effective to improve the insomnia while minimizing next day residual sedation.

3. The method of claim 1, wherein the oral formulation comprises one or more tablets.

4. The method of claim 3, wherein each tablet comprises a dosage of doxepin of 3 mg.

5. The method of claim 1, wherein the oral formulation comprises one or more capsules.

6. The method of claim 1, wherein the patient has difficulty staying asleep during the final 45 minutes of an 8-hour sleep period.

7. The method of claim 1, wherein the patient has difficulty staying asleep during the final 30 minutes of an 8-hour sleep period.

8. The method of claim 1, wherein administering the formulation is effective to decrease wake time after sleep (WTAS).

9. The method of claim 1, wherein administering the formulation is effective to decrease wake after sleep onset (WASO).

10. The method of claim 1, wherein administering the formulation is effective to decrease latency to sleep onset (LSO).

11. The method of claim 1, wherein administering the formulation is effective to increase sleep efficiency (SE).

12. The method of claim 1, wherein administering the formulation is effective to increase total sleep time (TST).

13. The method of claim 1, further comprising administering an oral formulation comprising doxepin or a pharmaceutically acceptable salt thereof to a second patient in need thereof, wherein the second patient is aged 65 years or older, wherein the oral formulation comprises one or more tablets or one or more capsules for a total dosage of doxepin of 3 mg, and wherein the oral formulation is administered prior to bedtime.

* * * * *